(12) United States Patent
Khokhlov et al.

(10) Patent No.: US 9,508,938 B2
(45) Date of Patent: Nov. 29, 2016

(54) ORGANIC COMPOUND AND PHOTOVOLTAIC DEVICE COMPRISING THE SAME

(71) Applicant: Cryscade Solar Ltd, Nicosia (CY)

(72) Inventors: Pavel Khokhlov, Belmont, CA (US); Pavel Ivan Lazarev, Menlo Park, CA (US); Alexey Nokel, Moscow (RU)

(73) Assignee: Cryscade Solar Limited, Nicosia (CY)

( * ) Notice: Subject to any disclaimer, the term of this patent is extended or adjusted under 35 U.S.C. 154(b) by 0 days.

(21) Appl. No.: 14/885,624

(22) Filed: Oct. 16, 2015

(65) Prior Publication Data
US 2016/0043328 A1   Feb. 11, 2016

Related U.S. Application Data

(62) Division of application No. 13/414,657, filed on Mar. 7, 2012, now Pat. No. 9,193,727.

(60) Provisional application No. 61/451,593, filed on Mar. 10, 2011.

(51) Int. Cl.
*C07D 471/00* (2006.01)
*H01L 51/00* (2006.01)
(Continued)

(52) U.S. Cl.
CPC ......... *H01L 51/0072* (2013.01); *C07D 241/46* (2013.01); *C07D 471/06* (2013.01);
(Continued)

(58) Field of Classification Search
CPC  C07D 471/06; C07D 241/46; C07D 495/14; C07D 498/22; H01L 51/46; H01L 31/0224
USPC ................. 546/37; 544/31, 99, 347
See application file for complete search history.

(56) References Cited

U.S. PATENT DOCUMENTS

| | | |
|---|---|---|
| 3,639,430 A | 2/1972 | Altermatt |
| 5,539,100 A | 7/1996 | Wasielewski |

(Continued)

FOREIGN PATENT DOCUMENTS

| | | |
|---|---|---|
| CH | 508010 A | 5/1971 |
| CN | 101659664 A | 3/2010 |

(Continued)

OTHER PUBLICATIONS

Destrade, et al., Mol. Cryst. Liq. Cryst. 1984, 106, p. 121.
(Continued)

*Primary Examiner* — Shane Fang
(74) *Attorney, Agent, or Firm* — FisherBroyles LLP; Adam Whiting

(57) ABSTRACT

The present invention provides a organic compound of the general structural formula I and photovoltaic device and photovoltaic layer comprising thereof

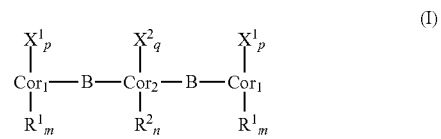

(I)

Said organic compound forms rod-dike supramolecules and absorbs electromagnetic radiation in at least one predetermined spectral subrange within a wavelength range from 400 to 3000 nm with excitation of electron-hole pairs. The polycyclic core $Cor_1$, the bridging group B, and the polycyclic core $Cor_2$ form a molecular system selected from the list comprising donor-bridge-acceptor-bridge-donor and acceptor-bridge-donor-bridge-acceptor in which a dissociation of excited electron-hole pairs is carried out. A solution of the organic compound or its salt forms a solid photovoltaic layer on a substrate.

18 Claims, 3 Drawing Sheets

(51) Int. Cl.
| | |
|---|---|
| C07D 241/46 | (2006.01) |
| C07D 471/06 | (2006.01) |
| C07D 471/22 | (2006.01) |
| C07D 487/16 | (2006.01) |
| C07D 493/06 | (2006.01) |
| C07D 495/14 | (2006.01) |
| C07D 498/04 | (2006.01) |
| C07D 498/22 | (2006.01) |
| C07D 513/14 | (2006.01) |
| C07D 519/00 | (2006.01) |
| C09B 5/62 | (2006.01) |
| H01L 51/42 | (2006.01) |

(52) U.S. Cl.
CPC ........... *C07D471/22* (2013.01); *C07D 487/16* (2013.01); *C07D 493/06* (2013.01); *C07D 495/14* (2013.01); *C07D 498/04* (2013.01); *C07D 498/22* (2013.01); *C07D 513/14* (2013.01); *C07D 519/00* (2013.01); *C09B 5/62* (2013.01); *H01L 51/0053* (2013.01); *H01L 51/0055* (2013.01); *H01L 51/0058* (2013.01); *H01L 51/0071* (2013.01); *H01L 51/42* (2013.01); *Y02E 10/549* (2013.01)

(56) References Cited

U.S. PATENT DOCUMENTS

| | | |
|---|---|---|
| 2008/0185577 A1 | 8/2008 | Facchetti |
| 2008/0249309 A1 | 10/2008 | Facchetti et al. |
| 2008/0287678 A1 | 11/2008 | Konemann |

FOREIGN PATENT DOCUMENTS

| | | |
|---|---|---|
| CN | 101665492 A | 10/2010 |
| DE | 950801 C | 10/1956 |
| DE | 1569841 A | 8/1970 |
| DE | 1569841 B1 | 8/1970 |
| JP | H06-151928 A | 5/1994 |
| JP | 7072332 A | 3/1995 |
| WO | 0031040 A | 6/2000 |
| WO | 2008038047 A | 4/2008 |
| WO | 2009141288 A2 | 11/2009 |

OTHER PUBLICATIONS

Lei et al. "Calamatic Liquid Crystal Blends for Organic Photovoltaics", Proc. of SPIE, vol. 7052, 2008, pp. 705214-1-705214-9.

Eversloh et al., "Core-Extended Peryleneetracarboxdiimides: The Homologous Series of Coronene Tetracarboxdiimides", Organic Letters 2011, vol. 13, No. 15, pp. 4148-4150.

Dittmer et al., "Crystal Network Formation in Organic Solar Cells", Synthetic Metals, vol. 102, pp. 879-880 (1999).

Bullock et al: "Photoinitiated Charge Transport Through pi-Stacked Electron Conduits in Supramolecular Ordered Assemblies of Donor-Acceptor Triads", Journal of the American Chemical Society, vol. 131, No. 33, Aug. 25, 2009 (Aug. 26, 2009), pp. 11919-11929.

Klaus Petritsch, PhD Thesis, "Organic Solar Cell Architectures", Cambridge and Graz, Jul. 2000, Chapter 4, Double Layer Devices, p. 67.

Schmidt-Mende, et al., "Self-Organised Discotic Liquid Crystals for High-Efficiency Organic Photovoltaics", Science 2001, vol. 293, p. 1119.

Ahrens et al., "Self-Assembly of Supramolecular Light-Harvesting Arrays from Covalent Multi-Chromophore Perylene-3,4:9,10-bis(dicarboximide) Building Blocks", Journal of the American Chemical Soceity, vol. 126, No. 26, Jul. 1, 2004, pp. 8284-8294.

Weil et al. "The Rylene Colorant Family-Tailored Nanoemitters for Photonics Research and Applications", Angew. Chem. Int. Ed., 2010—Wiley, Weinheim, vol. 49, pp. 9068-9093.

Lv et al., "Aggregation-Enhanced Emission in Gold Nanoparticles Protected by Tetradentate Perylene Derivative, Langmuir," 2009 , 25 (19), 11351-11357.

Pan et al., "Synthesis of carrier-transporting dendrimers with perylenebis (dicarboximide) as a luminescent core," European Journal of Organic Chemistry, 2006, (4) , 986-1001.

Lu et al., "Synthesis, characterization and photovoltaic application of N, N'-bisfluorenyl substituted perylene bisimide," Solar Energy Materials & Solar Cells, 2010, 94 (12), 2036-2041.

Gao et al., "Synthesis and near-infrared characteristics of novel perylene bisimide dyes bay-functionalized with haphthalimide chromophores," Chinese Chemical Letters, 2007, 18(3), 283-286.

Zhu et al., "Novel triad dyes with wide spectral response for SnO2 nanoporous electrode," Chemistry Letters, 2000, (7), 778-779.

ORGANIC COMPOUND AND PHOTOVOLTAIC DEVICE COMPRISING THE SAME

FIELD OF THE INVENTION

The present invention relates generally to the field of organic chemistry and particularly to an organic compounds and photovoltaic devices intended for transforming energy of light and, specifically, for converting solar energy into electric energy.

BACKGROUND OF THE INVENTION

Development of solar cells or photovoltaic (PV) devices based on organic materials has become an important research field with substantial application perspectives. Features of these devices such as versatility and compatibility with flexible substrates combined with low-cost and large-area production provide them with advantages compared to conventional inorganic silicon-based solar cells. Among various organic semiconductors, liquid crystals (LCs) forming 2D columnar structures (see, C. Destrade, P. Foucher, H. Gasparroux, N. H. Tinh, A. M. Levelut, J. Malthete, *Mol. Cryst. Liq. Cryst.* 1984, 106, 121) are promising materials for PV applications (see, L. Schmidt-Mende, A. Fechtenkötter, K. Müllen, E. Moons, R. H. Friend, J. D. Mackenzie, *Science* 2001, 293, 1119). In spite of much effort, the realization of efficient organic solar cells remains a major scientific challenge. There is a known photovoltaic converter based on poly(2-methoxy-5-(2'-ethyl-hexyioxy)-p-phenylenevinylene) (MEH-PPV) copolymer and a perylene-phenyl-ethyl-imide derivative (PPEI) (see J. J. Dittmer et al., Synthetic Metals, Vol. 102,879-880 (1999)). In this system, MEH-PPV acts as a hole acceptor, and PPEI acts as an electron acceptor (hole donor). Excitons which are photogenerated in the organic semiconductor subsequently decay into free charge carriers (electrons and holes) at the interface between the donor and acceptor components. Introduction of PPEI significantly increases the external quantum efficiency of photovoltaic devices employing this system. The PPEI particles are distributed in the MEH-PPV matrix volume over a distance equal to the exciton diffusion lenth (~9 nm). Thus, a charge separation is stimulated in thin-film MEH-PPV structures in presence of PPEI.

Another known photovoltaic cell comprises the first layer of an organic electron donor material in contact with the second layer made of an organic electron acceptor material (Klaus Petritsch, PhD Thesis, "Organic Solar Cell Architectures", Cambridge and Graz, July 2000. Chapter 4, Double Layer Devices, p. 67). These electron donor and electron acceptor materials are capable of absorbing light in a wavelength range from 350 to 1000 nm, and these materials are capable of forming a rectifying junction when contact with each other. The cell is provided with electrodes forming Ohmic contacts at least with a part of the surface of organic layers. A distinctive feature of said photovoltaic cell is that the organic materials employed contain organic compounds with generally planar polycyclic nuclei. These compounds are capable of forming a layer structure of a total thickness not exceeding 0.5 micron.

Organic layers of the above referenced materials do not possess crystalline structure which is a disadvantage for the photovoltaic devices. For this reason the mobility of electrons and holes in these layers is much lower as compared to that in the same bulk crystalline materials. As a result, electrons and holes do not leave the active region of a semiconductor structure during the exciton lifetime and recombine. Such electron-hole pairs do not contribute to the photocurrent, and the photovoltaic conversion efficiency decreases. In addition, a decrease in the electron and hole mobility leads to an increase in the resistivity of the material and, hence, in the serial resistance of the photovoltaic device. This implies increase of Ohmic losses and additional decrease in the photovoltaic conversion efficiency. Another disadvantage of the aforementioned photovoltaic devices is that the non-crystalline materials possess extremely small diffusion length of photogenerated excitons. This requires using photovoltaic structures of very thin layers of thickness comparable with the exciton diffusion length, and which also decreases both external and internal quantum efficiency of the photovoltaic devices.

The disclosed organic compounds and photovoltaic devices on their base are intended to overcome the disadvantages of the organic compounds and photovoltaic devices of the prior art.

Definitions of various terms used in the description and claims of the present invention are listed below.

The term "space group $C_{2v}$" is illustrated in FIG. 1 and indicates that a molecule or molecular part has a 2-fold rotation axis AA' and a mirror plane $M_1$ parallel to the axis of rotation. Combination of the 2-fold axis and mirror plane gives one more mirror plate $M_2$ which is parallel to the rotation axis and perpendicular to the first mirror plane $M_1$.

The term "space group $D_{2h}$" is illustrated in FIG. 2 and indicates that a molecule or molecular part has two 2-fold rotation axes AA' and BB' perpendicular to each other and mirror plane $M_1$ perpendicular to one of them. This combination of the symmetry elements gives two additional mirror planes $M_2$ and $M_3$ perpendicular to each other and perpendicular to the initial mirror plane. It also provides one additional 2-fold, axis CC' which is perpendicular to the initial 2-fold axes. An inversion center O is in the center of the molecular structure.

SUMMARY OF THE INVENTION

The present invention provides an organic compound of the general structural formula I:

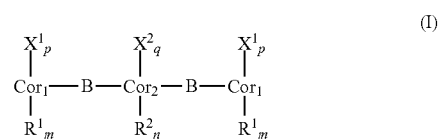

(I)

where $Cor_1$ is a polycyclic core of a first type; $Cor_2$ is a polycyclic core of a second type; B is a bridging group providing a bond of the polycyclic core $Cor_1$ with the polycyclic core $Cor_2$ via covalent chemical bonds; $R^1$ and $R^2$ are molecular groups providing solubility of the organic compound in a suitable solvent; m is 1, 2, 3 or 4; n is 0, 1, 2, 3 or 4; $X^1$ $X^2$ are modifying groups which modify energy levels HOMO and LUMO of the polycyclic cores $Cor_1$ and $Core_2$ accordingly; p is 0, 1, 2; and q is 0, 1, 2. Said organic compound forms rod-like supramolecules because of π-π-interaction and absorbs electromagnetic radiation in at least one predetermined spectral subrange within a wavelength range from 400 to 3000 nm with excitation of electron-hole pairs. The polycyclic core $Cor_1$, bridging group B, and polycyclic core $Cor_2$ form a molecular system. $Cor_1$-B-$Cor_2$-B-$Cor_1$ selected from the list comprising donor-bridge-acceptor-bridge-donor and acceptor-bridge-donor-bridge-acceptor in which a dissociation of excited electron-hole pairs is carried out.

In a further aspect, the present invention provides a photovoltaic device comprising a first and a second electrodes and at least one photovoltaic layer having a front surface and a rear surface. Said photovoltaic layer comprises at least one organic compound having a general structural formula I:

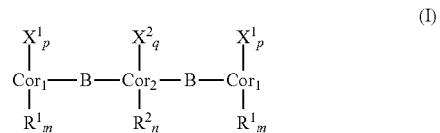
(I)

where $Cor_1$ is a polycyclic core of a first type; $Cor_2$ is a polycyclic core of a second type; B is a bridging group providing a bond of the polycyclic core $Cor_1$ with the polycyclic core $Cor_2$ via covalent chemical bonds; $R^1$ and $R^2$ are molecular groups providing solubility of the organic compound in a suitable solvent; m is 1, 2, 3 or 4; n is 0, 1, 2, 3 or 4; $X^1$ and $X^2$ are modifying groups which modify energy levels HOMO and LUMO of the polycyclic cores $Cor_1$ and $Cor_2$ accordingly; p is 0, 1, 2; q is 0, 1, 2. Said organic compound forms rod-like supramolecules because of π-π-interaction and absorbs electromagnetic radiation in at least one predetermined spectral subrange within a wavelength range from 400 to 3000 nm with excitation of electron-hole pairs. The polycyclic core $Cor_1$, bridging group B, and polycyclic core $Cor_2$ form a molecular system $Cor_1$-B-$Cor_2$-B-$Cor_1$ selected from the list comprising donor-bridge-acceptor-bridge-donor and acceptor- bridge-donor-bridge-acceptor in which a dissociation of excited electron-hole pairs is carried out. The organic compound homeotropically aligned in respect to the photovoltaic layer surface and the polycyclic cores $Cor_1$ and $Cor_2$ assemble into a π-π stack of a first type and a π-π stack of a second type respectively. The stacks of one type realize electron transport, the stacks of another type realize hole transport and said stacks are electrically isolated from each other by the molecular groups $R^1$ and $R^2$.

In still further aspect, the present invention provides a photovoltaic layer comprising at least one organic compound having a general structural formula I:

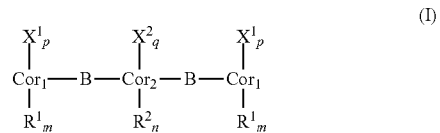
(I)

where $Cor_1$ is a polycyclic core of a first type; $Cor_2$ is a polycyclic core of a second type; B is a bridging group providing a bond of the polycyclic core $Cor_1$ with the polycyclic core $Cor_2$ via covalent chemical bonds; $R^1$ and $R^2$ are molecular groups providing solubility of the organic compound in a suitable solvent; m is 1, 2, 3 or 4; n is 0, 1, 2, 3 or 4; $X^1$ and $X^2$ are modifying groups which modify energy levels HOMO and LUMO of the polycyclic cores $Cor_1$ and $Cor_2$ accordingly; p is 0, 1, 2; q is 0, 1, 2. Said organic compound forms rod-like supramolecules because of π-π-interaction and absorbs electromagnetic radiation in at least one predetermined spectral subrange within a wavelength range from 400 to 3000 nm with excitation of electron-hole pairs. The polycyclic core $Cor_1$, the bridging group B, and the polycyclic core $Cor_2$ form a molecular system $Cor_1$-B-$Cor_2$-B-$Cor_1$ selected from the list comprising donor-bridge-acceptor-bridge-donor and acceptor-bridge-donor-bridge-acceptor in which a dissociation of excited electron-hole pairs is carried out. The organic compound homeotropically aligned in respect to the photovoltaic layer surface and the polycyclic cores $Cor_1$ and $Cor_2$ assemble into a π-π stack of a first type and a π-π stack of a second type respectively. The stacks of one type realize electron transport, the stacks of another type realize hole transport and said stacks are electrically isolated from each other by the molecular groups $R^1$ and $R^2$.

BRIEF DESCRIPTION OF THE DRAWINGS

These and various other features and advantages of the present invention will become better understood upon reading of the following detailed description in conjunction with the accompanying drawings and the appended claims provided below, where:

DETAILED DESCRIPTION OF THE INVENTION

Figure 1:
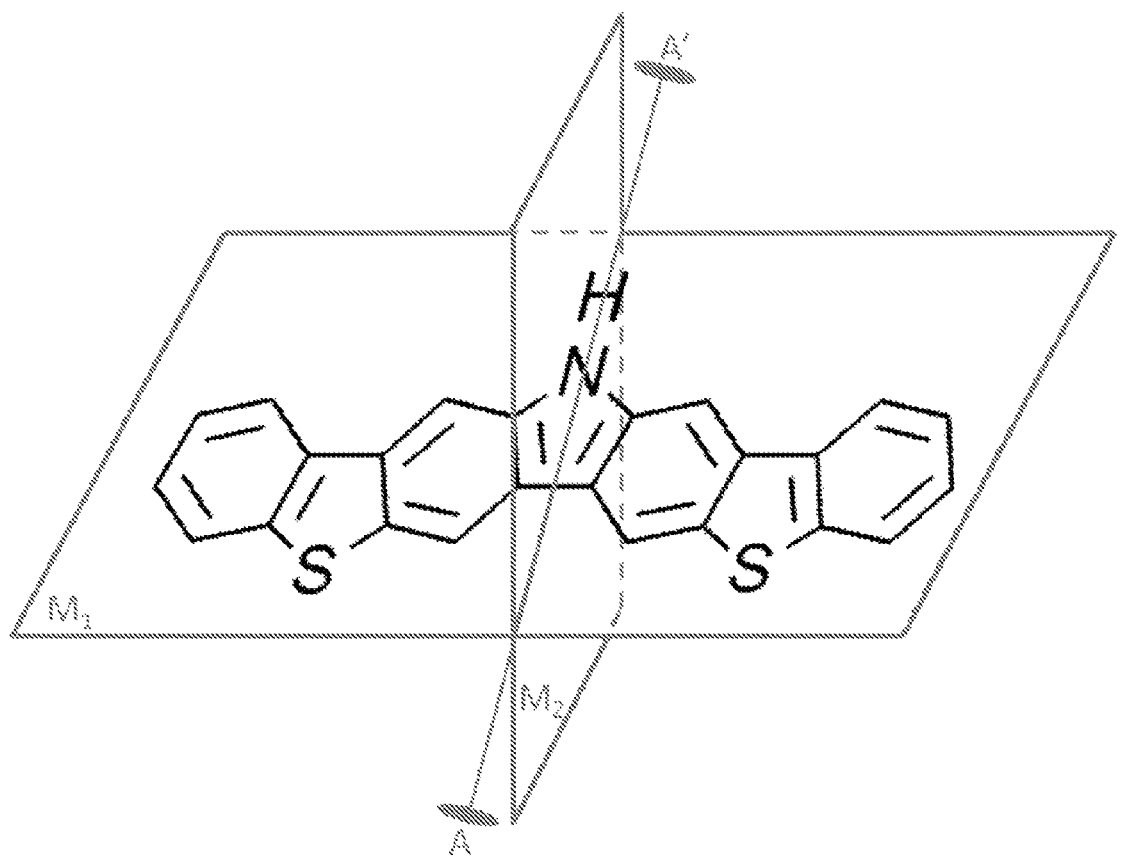
FIG. 1 illustrates a space group $C_{2v}$.
Figure 2:
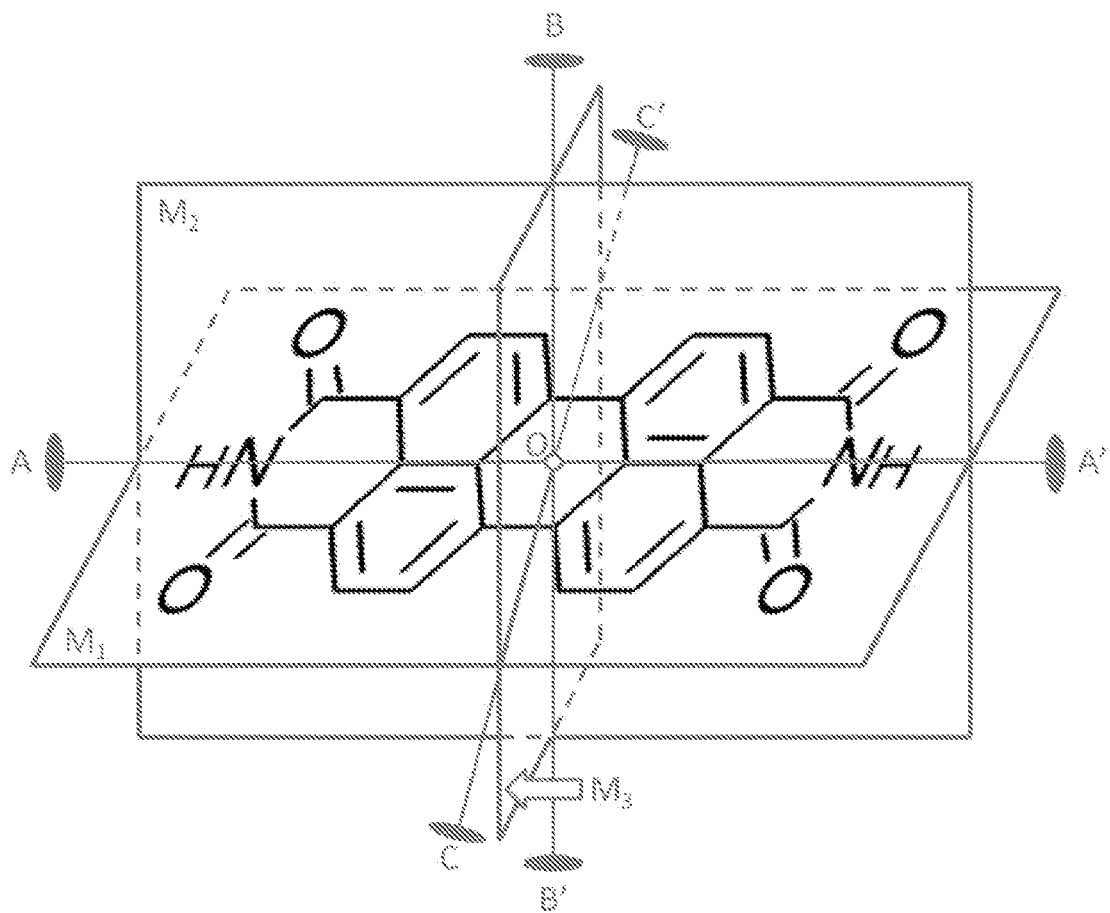
FIG. 2 illustrates a space group $D_{2h}$.

The general description of the present invention having been made, a further understanding can be obtained by reference to the specific embodiments, which are given herein only for the purpose of illustration and are not intended to limit the scope of the appended claims.

The present invention provides the organic compound as disclosed hereinabove. A solution of the organic compound or its salt forms a solid photovoltaic layer on a substrate. In one embodiment of the disclosed organic compound at least one of the polycyclic cores is a heterocyclic core. In one embodiment of the disclosed compound, the providing solubility groups $R^1$ and $R^2$ are independently selected from the list comprising —COOH, —SO$_3$H, and —H$_2$PO$_3$ for water or water-miscible solvent; and linear and branched ($C_1C_{35}$) alkyl, ($C_2$-$C_{35}$)alkenyl, and ($C_2$-$C_{35}$)alkinyl, substituted alkyl, substituted aryl, and any combination thereof for organic solvent, wherein these groups are connected with the cores $Cor_1$ and $Cor_2$ directly or via a spacer selected from the list comprising aryl, —C(O)—, —C(O)O—, —C(O)—NH—, —S(O$_2$)NH—, —O—, —CH$_2$O—, —NH—, >N—, and any combination thereof. In another embodiment of the compound, at least one of the bridging groups B is selected from the list comprising p-phenylene (Ph$_p$) oligomer, where p is 1, 2, 3, 4 or 5; 2,7-ogliofluorene (Fl$_s$) oligomer, where s is 1, 2, 3, or 4, and alkylen groups —(CH$_2$)$_2$—, where j is 1, 2, 3, or 4. In yet another embodiment of the compound, the modifying groups $X^1$ and $X^2$ are independently selected from the list comprising H, Cl, Br, F, OH, NO$_2$, NO, and NH$_2$. In still another embodiment of the compound, at least one of the polycycilc cores $Cor_1$ and $Cor_2$ comprises heteroatoms selected from the list comprising nitrogen, oxygen, sulfur, and any combination thereof.

In yet another embodiment of the compound, the polycyclic core $Cor_2$ is selected from the list comprising structures from 1 to 5 shown in Table 1.

TABLE 1
Examples of the polycyclic core Cor$_2$
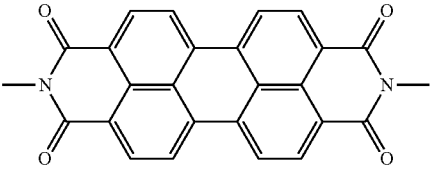
1
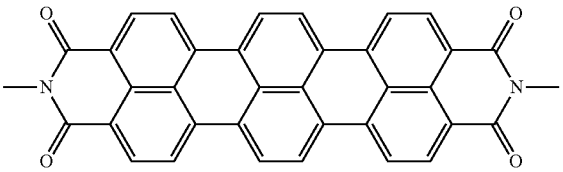
2
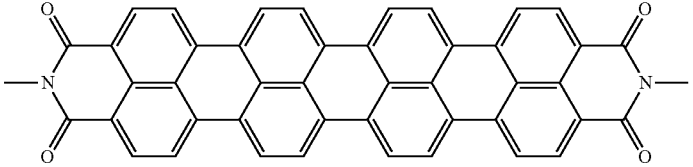
3
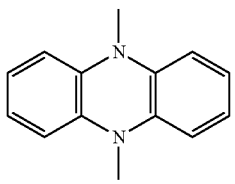 [SMILES: CN1c2ccccc2N(C)c2ccccc21]
4
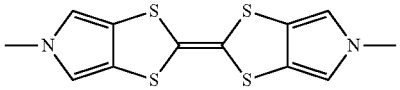
5
In still another embodiment of the compound, the polycyclic core Cor$_1$ is selected from the list comprising structures from 6 to 20 shown in Table 2.
TABLE 2
Examples of the polycyclic core Cor$_1$
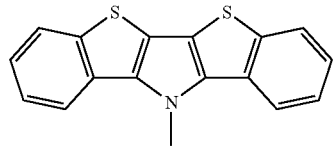
6
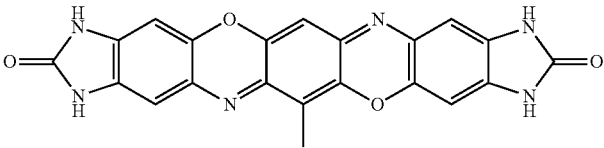 [SMILES: Cc1c2c(cc3c1=Nc1cc4[nH]c(=O)[nH]c4cc1O3)=Nc1cc3[nH]c(=O)[nH]c3cc1O2]
7

TABLE 2-continued
Examples of the polycyclic core Cor₁
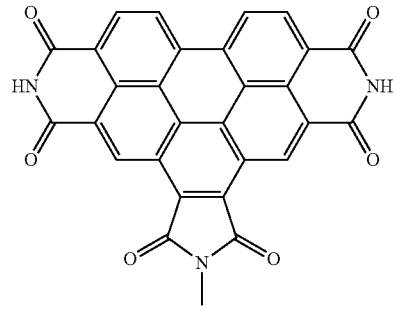 [SMILES: Cn1c(=O)c2c3cc4c(=O)[nH]c(=O)c5ccc6c7ccc8c(=O)[nH]c(=O)c9cc(c2c1=O)c(c7c89)c3c6c54]
8
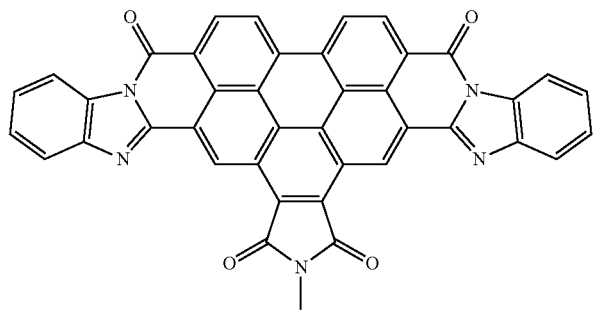 [SMILES: Cn1c(=O)c2c3cc4c5c(ccc6c7ccc8c(=O)n9c%10ccccc%10nc9c9cc(c2c1=O)c(c7c89)c3c65)c(=O)n1c2ccccc2nc41]
9
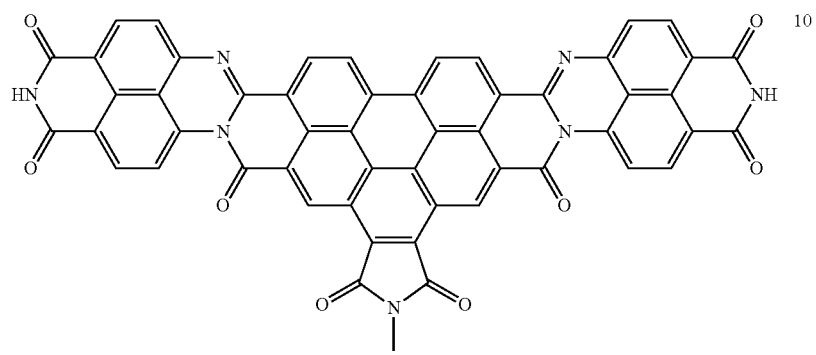
10
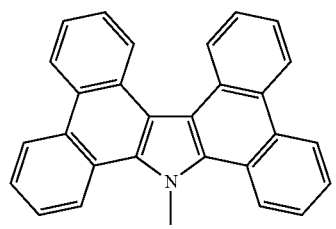 [SMILES: Cn1c2c3ccccc3c3ccccc3c2c2c3ccccc3c3ccccc3c21]
11
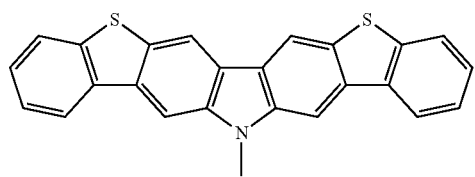 [SMILES: Cn1c2cc3c(cc2c2cc4sc5ccccc5c4cc21)sc1ccccc13]
12

TABLE 2-continued
Examples of the polycyclic core Cor$_1$
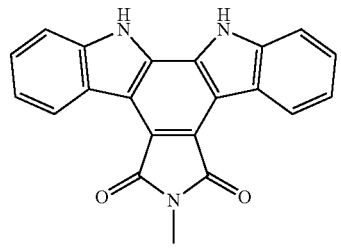 [SMILES: CN1C(=O)c2c(c3c4ccccc4[nH]c3c3[nH]c4ccccc4c23)C1=O]
13
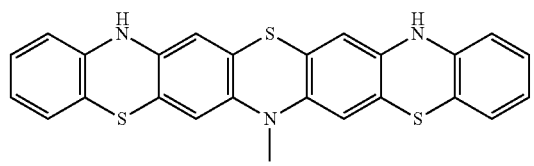 [SMILES: Cn1c2cc3sc4ccccc4[nH]c3cc2sc2cc3[nH]c4ccccc4sc3cc21]
14
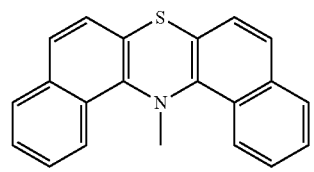 [SMILES: CN1c2c(ccc3ccccc23)Sc2ccc3ccccc3c21]
15
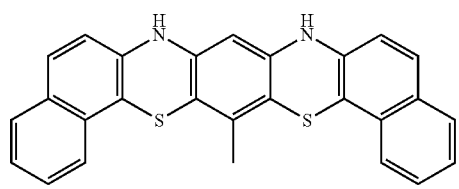 [SMILES: Cc1c2sc3c(ccc4ccccc43)[nH]c2cc2[nH]c3ccc4ccccc4c3sc12]
16
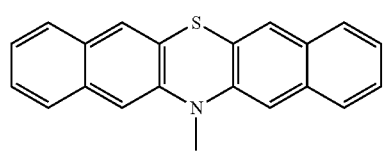 [SMILES: CN1c2cc3ccccc3cc2Sc2cc3ccccc3cc21]
17
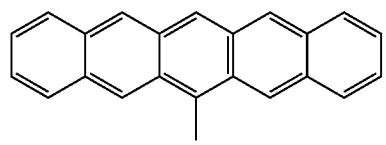 [SMILES: Cc1c2cc3ccccc3cc2cc2cc3ccccc3cc12]
18
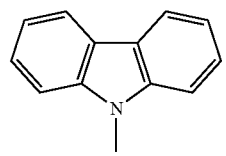
19
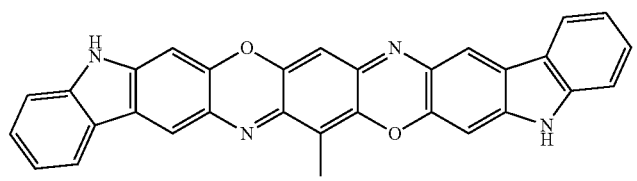 [SMILES: Cc1c2c(cc3c1=Nc1cc4c(cc1O3)[nH]c1ccccc14)=Nc1cc3c(cc1O2)[nH]c1ccccc13]
20

In one embodiment of the disclosed compound, the core $Cor_1$ possesses symmetry of the $C_{2s}$ or $D_{2h}$ space groups, and the core $Cor_2$ possesses symmetry of the $D_{2h}$ space group. In another embodiment of the disclosed compound, the molecular system $Cor_1$-B-$Cor_2$-B-$Cor_1$ possesses a symmetry of the $D_{2h}$ space group. In one embodiment of the compound, the energy levels of donors are correlated with energy levels of acceptor according to the following equations: $HOMO_A < HOMO_D \leq LUMO_A - 1$ eV and $LUMO_A < LUMO_D$.

In another embodiment of the present invention, perylene diimide serves as the acceptor core $Cor_2$ the bridging group B is selected from the list comprising phenyl and biphenyl, and the energy levels $HOMO_D$ and $LUMO_D$ of donor cores $Cor_1$ satisfy to the following conditions $-6.0$ eV$<HOMO_D<-5.5$ eV and $-4.0$ eV$<LUMO_D$.

In another embodiment of the present invention, the organic compound is selected from the list comprising structares from 21 to 26 shown in Table 3.

TABLE 3

Examples of the organic compound according to the present invention

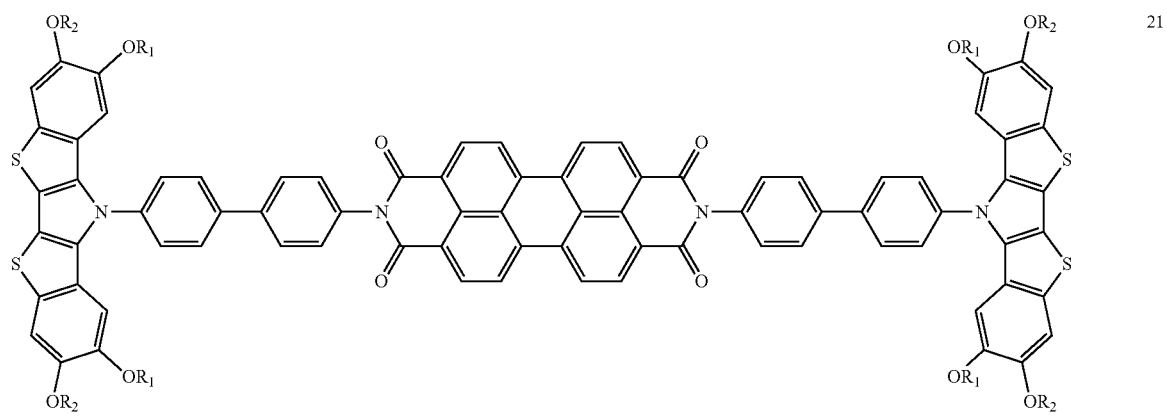

21

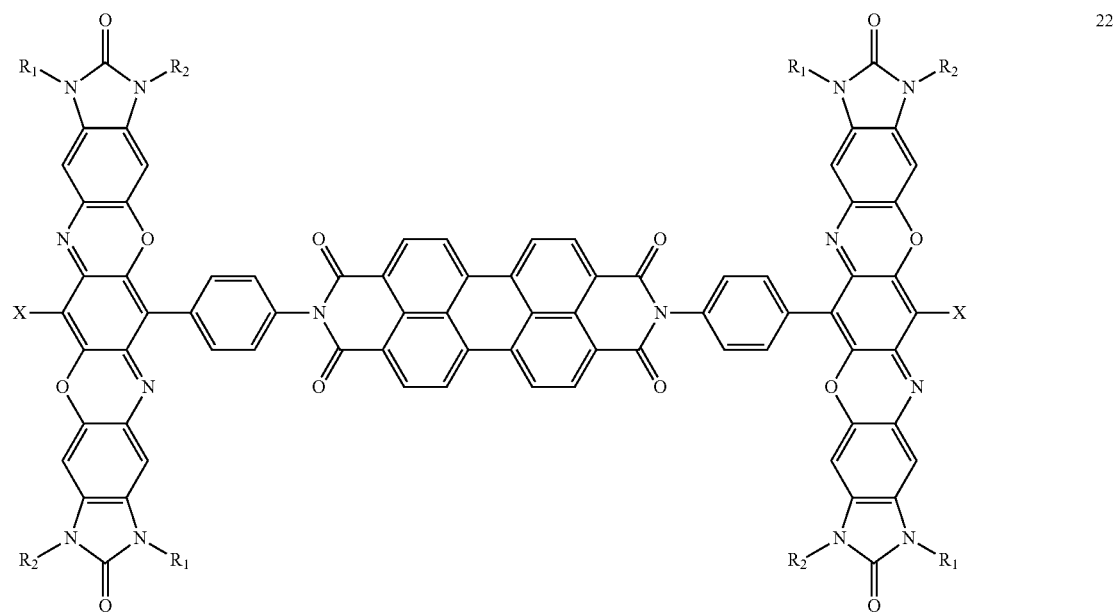

22

TABLE 3-continued
Examples of the organic compound according to the present invention
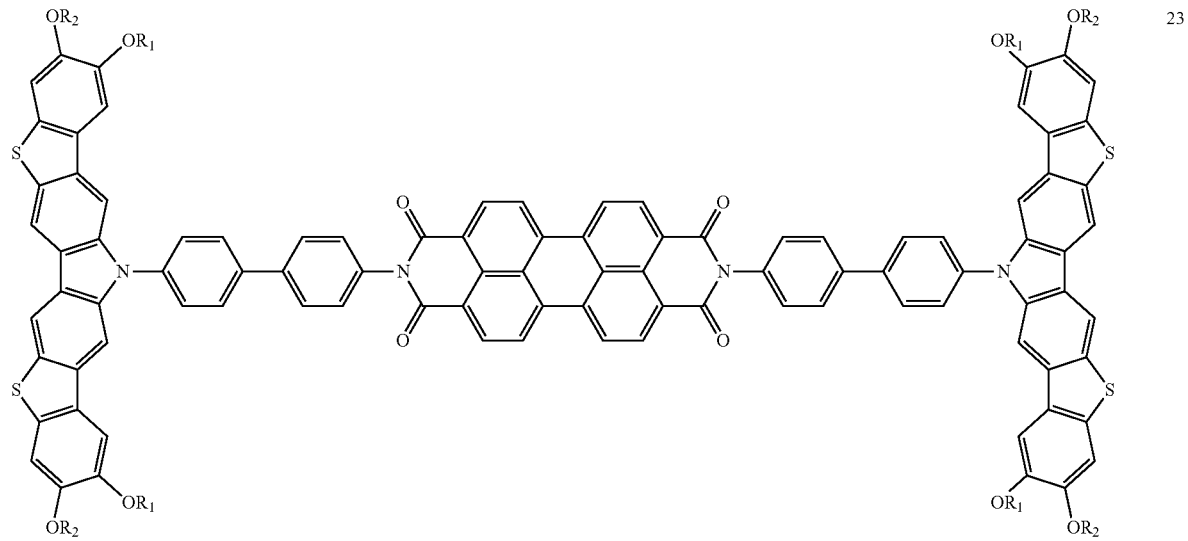
23
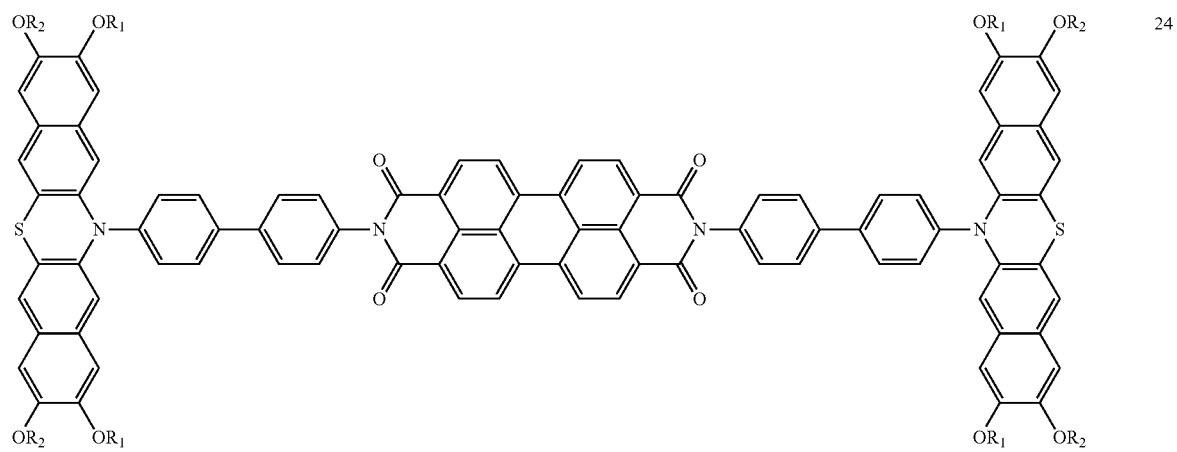
24
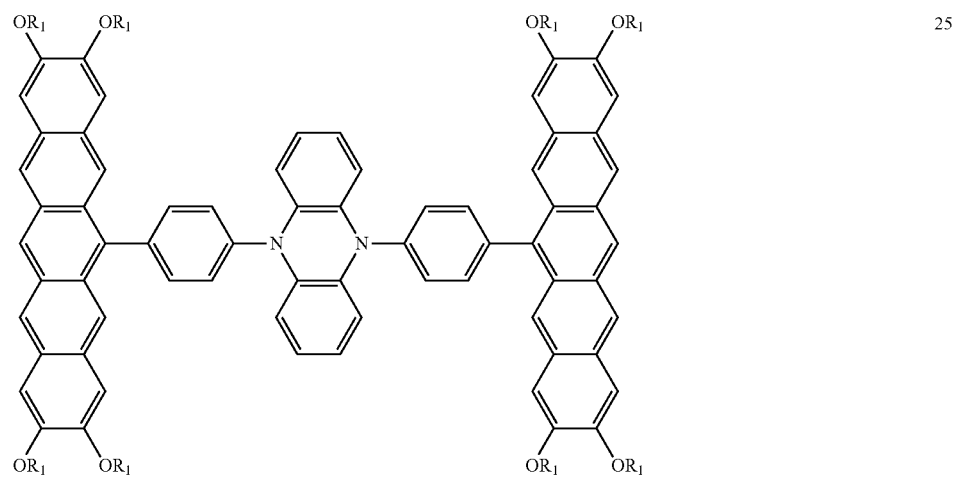
25

TABLE 3-continued

Examples of the organic compound according to the present invention

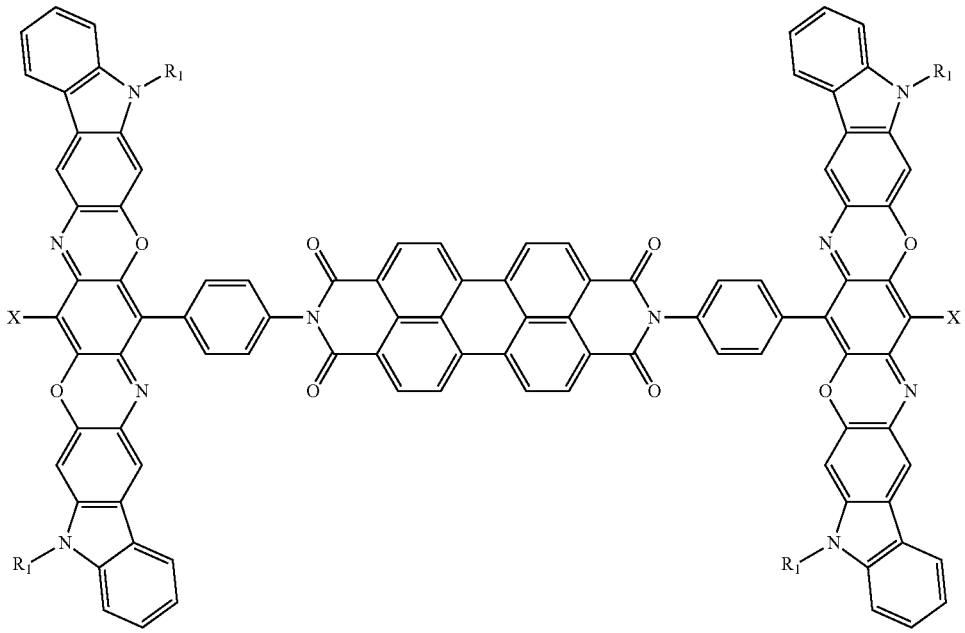

26 where R, R¹ and R² are linear and branched ($C_1$-$C_{35}$)alkyl, ($C_2$-$C_{35}$)alkenyl, and ($C_2$-$C_{35}$)alkinyl, substituted alkyl, substituted aryl, and any combination thereof; and X is Cl or Br.

In yet another embodiment of the disclosed compound, the suitable solvent is selected from the list comprising water, water-miscible solvent, ketones, carboxylic acids, hydrocarbons, cyclohydrocarbons, chlorohydrocarbons, alcohols, ethers, esters, and any combination thereof.

The present invention also provides the photovoltaic device as disclosed hereinabove. In one embodiment of the disclosed photovoltaic device, at least one of the polycyclic cores $Cor_1$ and $Cor_2$ is a heterocyclic core. In another embodiment of the disclosed photovoltaic device, the providing solubility groups R¹ and R² are independently selected from the list comprising —COOH, —SO₃H, and —H₂PO₃ for water or water-miscible solvent; and linear and branched ($C_1$-$C_{35}$)alkyl, ($C_2$-$C_{35}$)alkenyl, and ($C_2$-$C_{35}$)alkinyl, substituted alkyl, substituted aryl, and any combination thereof for organic solvent, wherein these groups are connected with the cores $Cor_1$ and $Cor_2$ directly or via a spacer selected from the list comprising aryl, —C(O)—, —C(O)O—, —C(O)—NH—, —(SO₂)NH—, —O—, —CH₂O—, —NH—, >N—, and any combination thereof. In yet another embodiment of the disclosed photovoltaic device, at least one of the bridging groups B is selected from the list comprising p-phenylene ($Ph_p$) oligomer, where p is 1, 2, 3, 4 or 5; 2,7-oligofluorene ($Fl_s$) oligomer, where s is 1, 2, 3, or 4; and alkylen groups —(CH₂)$_j$—, where j is 1, 2, 3, or 4. In still another embodiment of the disclosed photovoltaic device, the modifying groups X¹ and X² are selected from the list comprising H, Cl, Br, F, OH, NO₂, NO, and NH₂, In one embodiment of the disclosed photovoltaic device, at least one of the polycyclic cores $Cor_1$ and $Cor_2$ comprises hetero-atoms selected from the list comprising nitrogen, oxygen, sulfur, and any combination thereof. In still another embodiment of the disclosed photovoltaic device, the polycyclic core $Cor_2$ is selected from the list comprising structures from 1 to 5 shown in Table 1. In one embodiment of the disclosed photovoltaic device, the polycyclic core $Cor_1$ is selected from the list comprising structures from 6 to 20 shown in Table 2. In another embodiment of the disclosed photovoltaic device the polycyclic core $Cor_1$ possesses a symmetry of the $C_{2v}$ or $D_{2h}$ space group, and the $Cor_2$ possesses a symmetry of the $D_{2h}$ space group. In yet another embodiment of the disclosed photovoltaic device, the molecular system $Cor_1$-B-$Cor_2$-B-$Cor_1$ possesses a symmetry of the $D_{2h}$ space group. In another embodiment of the disclosed photovoltaic device, the energy levels of donors are correlated with energy levels of acceptor according to the following equations: $HOMO_A < HOMO_D \leq LUMO_A 1$ eV and $LUMO_A < LUMO_D$. In yet another embodiment of the photovoltaic device, perylene diimide serves as the acceptor core $Cor_2$, the bridging group B is selected from the list comprising phenyl and biphenyl, and the energy levels $HOMO_D$ and $LUMO_D$ of donor cores $Cor_1$ satisfy to the following conditions $-6.0$ eV $< HOMO_D < -5.5$ eV and $-4.0$ eV $< LUMO_D$. In yet another embodiment of the photovoltaic device, the compound is selected from the list comprising structures from 21 to 26 shown in Table3.

In one embodiment of the present invention, the disclosed photovoltaic device comprises the photovoltaic layer, the first electrode formed on at least part of the front surface of said photovoltaic layer, and the second electrode formed on at least part of the rear surface of said photovoltaic layer. In one embodiment of the disclosed photovoltaic device, the second electrode is a reflective electrode for the electromagnetic radiation incident upon the device. In another embodiment of the disclosed photovoltaic device, one said electrode is made of material with work function providing a hole-harvesting contact and a barrier contact for electrons, and another said electrode is made of material with work function providing a barrier contact for holes and an electron-harvesting contact. In yet another embodiment of the disclosed photovoltaic device, the electrode material is selected from the list comprising metals, ITO (indium tin oxide), carbon nanotube conductive coatings, PEDOT: PSS layers, phthalocyanines, LiF, and aluminium-doped zinc oxide. In still another embodiment of the disclosed photovoltaic device, one said electrode comprises an electron-acceptor layer contacting with the photovoltaic layer, and another said electrode comprises an electron-donor layer contacting with the photovoltaic layer. In one embodiment of the present invention, the disclosed photovoltaic device further comprises a substrate bearing said electrodes and said photovoltaic layer. In one embodiment of the disclosed photovoltaic device, the substrate is made of material selected from the list comprising a polymer and glass. In another embodiment of the disclosed photovoltaic device, the substrate is transparent for the incident electromagnetic radiation to which said device is sensitive.

Figure 3:
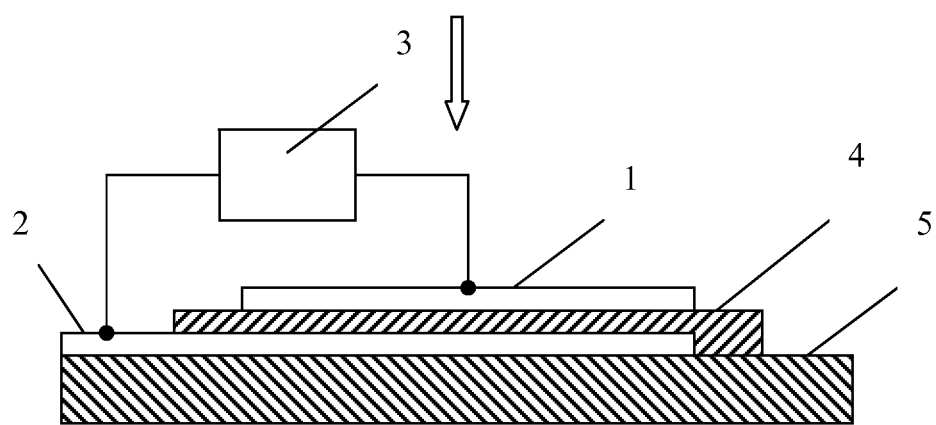
FIG. 3 shows the cross section of a photovoltaic device according to the present invention.

FIG. 3 presents a schematic diagram of the disclosed photovoltaic device, based on a photovoltaic layer (4) located between the first electrode (1) and the second electrode (2). The first electrode is made of material with work function providing a hole-harvesting contact and a barrier contact for electrons, and the second electrode is made of material with work function providing a barrier contact for holes and an electron-harvesting contact. The electrode material may be selected from the list comprising metals, ITO (indium tin oxide), carbon nanotube conductive coatings, PEDOT; PSS layers, phthalocyanines, LiF, and aluminium-doped zinc oxide. At least one of said electrodes is transparent for the incident electromagnetic radiation to which said photovoltaic layer is sensitive so the first electrode shown in FIG. 3 is transparent. Said photovoltaic layer (4) comprises the homeotropically aligned in respect to the surface of the photovoltaic layer organic compound which forms rod-like supramolecules. The rod-like supramolecules are formed by means of π-π-interaction of the single-type polycyclic cores providing different current-conducting-paths with electron and hole conductivity respectively. These current-conducting-paths are electrically isolated among themselves due to the groups providing solubility of the organic compound. The entire structure is formed on a substrate (5) and the electrodes are connected to a resistive load (3). The substrate is made of material selected from the list comprising a polymer and glass.

In one embodiment of the present invention, the photovoltaic device further comprises two or more said photovoltaic layers, wherein said photovoltaic layers comprise different organic compounds having the general structural formula I, and ensuring absorption of electromagnetic radiation in the same or different spectral subranges within a wavelength range from 400 to 3000 nm.

The present invention provides the photovoltaic layer as disclosed hereinabove. In one embodiment of the disclosed photovoltaic layer, at least one of the polycyclic cores $Cor_1$ and $Cor_2$ is a heterocyclic core. In another embodiment of the disclosed photovoltaic layer, the providing solubility groups $R^1$ and $R^2$ are independently selected from the list comprising —COOH, —SO$_3$H, and —H$_2$PO$_3$ for water or water-miscible solvent; and linear and branched ($C_1$-$C_{35}$) alkyl, ($C_2$-$C_{35}$)alkenyl, and ($C_2$-$C_{35}$)alkinyl, substituted alkyl, substituted aryl, and any combination thereof for organic solvent, wherein these groups are connected with the cores $Cor_1$ and $Cor_2$ directly or via a spacer selected from the list comprising aryl, —C(O)—, —C(O)O—, —C(O)—NH—, —(SO$_2$)NH—, —O—, —CH$_2$O—, —NH—, >N—, and any combination thereof. In yet another embodiment of the disclosed photovoltaic layer, at least one of the bridging groups B is selected from the list comprising p-phenylene ($Ph_p$) oligomer, where p is 1, 2, 3, 4 or 5; 2,7-oligofluorene ($Fl_s$) oligomer, where s is 1, 2, 3, or 4; and alkylen groups —(CH$_2$)$_j$—, where j is 1, 2, 3, or 4. In still another embodiment of the disclosed photovoltaic layer, the modifying groups $X^1$ and $X^2$ are selected from the list comprising H, Cl, Br, F, OH, NO$_2$, NO, and NH$_2$. In one embodiment of the disclosed photovoltaic layer, at least one of the polycyclic cores $Co_1$ and $Cor_2$ comprises hetero-atoms selected from the list comprising nitrogen, oxygen, sulfur, and any combination thereof. In still another embodiment of the disclosed photovoltaic layer, the polycyclic core $Cor_2$ is selected from the list comprising structures from 1 to 5 shown in 1 Table 1. In one embodiment of the disclosed photovoltaic layer, the polycyclic core $Cor_1$ is selected from the list comprising structures from 6 to 20 shown in Table 2. In another embodiment of the disclosed photovoltaic layer the polycyclic core $Cor_1$ possesses a symmetry of the $C_{2v}$ or $D_{2h}$ space group, and the $Cor_2$ possesses a symmetry of the $D_{2h}$ space group. In yet another embodiment of the disclosed photovoltaic layer, the molecular system $Cor_1$-B-$Cor_2$-B-$Cor_1$ possesses a symmetry of the $D_2h$ space group. In another embodiment of the disclosed photovoltaic layer, the energy levels of donors are correlated with energy levels of acceptor according to the following equations: HOMO$_A$<HOMO$_D$≤LUMO$_A$1 eV and LUMO$_A$<LUMO$_D$. In yet another embodiment of the photovoltaic layer, perylene diimide serves as the acceptor cote $Cor_2$, the bridging group B is selected from the list comprising phenyl and biphenyl, and the energy levels HOMO$_D$ and LUMO$_D$ of donor cores. $Cor_1$ satisfy to the following conditions −6.0 eV<HOMO$_D$<−5.5 eV and −4.0 eV<LUMO$_D$. In yet another embodiment of the photovoltaic layer, the compound is selected from the list comprising structures from 21 to 26 shown in Table 3.

In order that the invention may be more readily understood, reference is made to the following examples, which are intended to be illustrative of the invention, but are not intended to be limiting the scope.

EXAMPLE 1

The Example describes synthesis of the organic compound according to the present invention, wherein perylene derivative (structural formula 1) serves as the polycyclic core $Cor_2$, carbazole (structural formula 19) serves as the polycyclic core Cor1, and phenyl serves as the bridging group B (Scheme 1).

Scheme 1

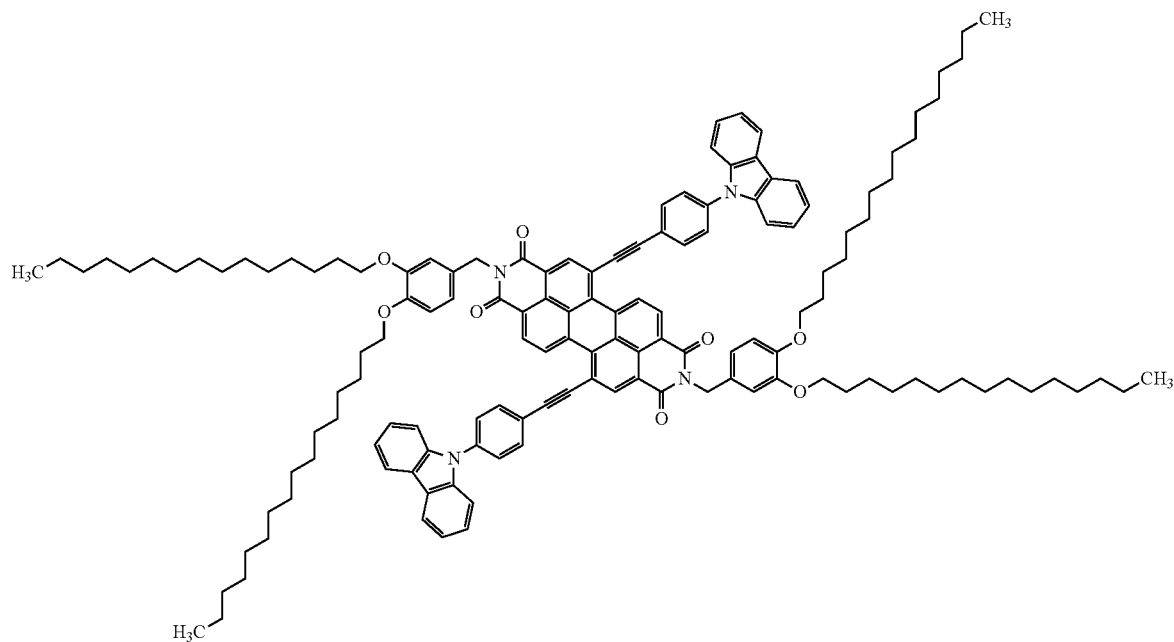

The organic compound was synthesized by Sonogashira reaction where N,N-bis[3,4-di(hexadecyloxy)benzyl]-1,7-dibromoperylene diimide is coupled with 9-(4-ethynylphenyl)carbazole.

1. Synthesis of 9-(4ethynylphenyl)carbazole (Scheme 2)

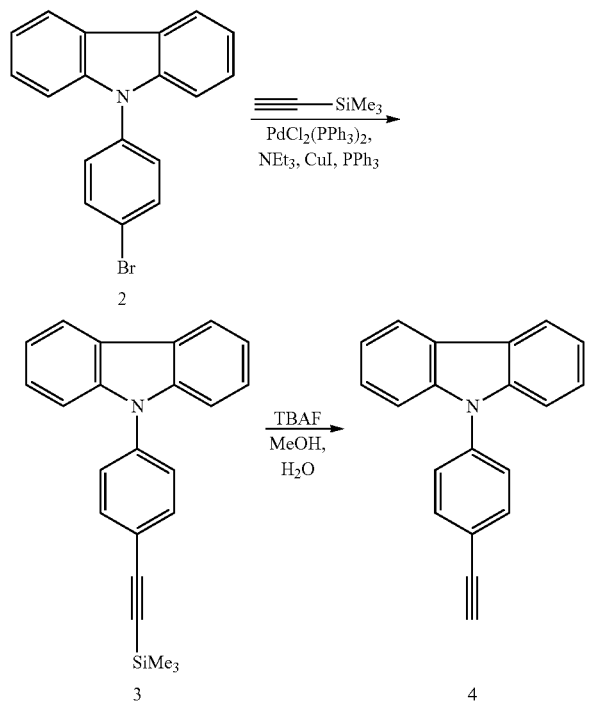

Scheme 2

Procedure:

Stage 1: A mixture of 9-(4-bromophenyl)carbazol (4.9 g, 15.3 mmol), trimethylsilylacetylene (2.17 mL), triphenylphosphine (0.19 g), and $Pd(PPh_3)_2Cl_2$ (0.12 g) in 60 mL triethylamine was degassed for 15 mm. Reaction mixture was boiled for 5 min, then CuI (0.12 g) was added. The resulted mixture was boiled for another 12 hours. A mixture was left at room temperature until completely cooled down, a precipitate wax filtered out. The filtrate was evaporated on a rotor evaporator, a residue was purified by column chromatography using hexane as an eluent, and recrystallized from heptane. The yield was 76%.

Stage 2: A mixture of carbazole 3 (2.0 g) and tetrabuthylammonium. flouride in 50 mL of anhydrous THF was stirred at room temperature for 12 hours, wherein the quantity of tetrabuthylammonium fluoride was selected as three moles of tetrabuthylammonium fluoride to one mole of carbazole. The resulting mixture was treated with 1N HCl (50 mL) and extracted with ether (2×50 mL). Organic layer was separated and dried over magnesium sulfate, then a solvent was removed under reduced pressure and the residue was recrystallized from hexane to produce carbazole 4. The yield of carbazole 4 was 65 %.

2. Synthesis of N,N-bis[3,4-di(hexadecyloxy)benzyl]-1,7-bis[4-carbazole-9--yl)phenyl4-ethynl] perylene diimide Synthesis of the organic compound 8 was comprising the direct coupling of previously obtained diimide 9 with ethynylcarbazole 4 in conditions of Sonogashira reaction (Scheme 3). The purity of diimide 9 was controlled by TLC, it was reprecipitated twice from $CHCl_3$-MeOH system and measured NMR $^1$H spectra.

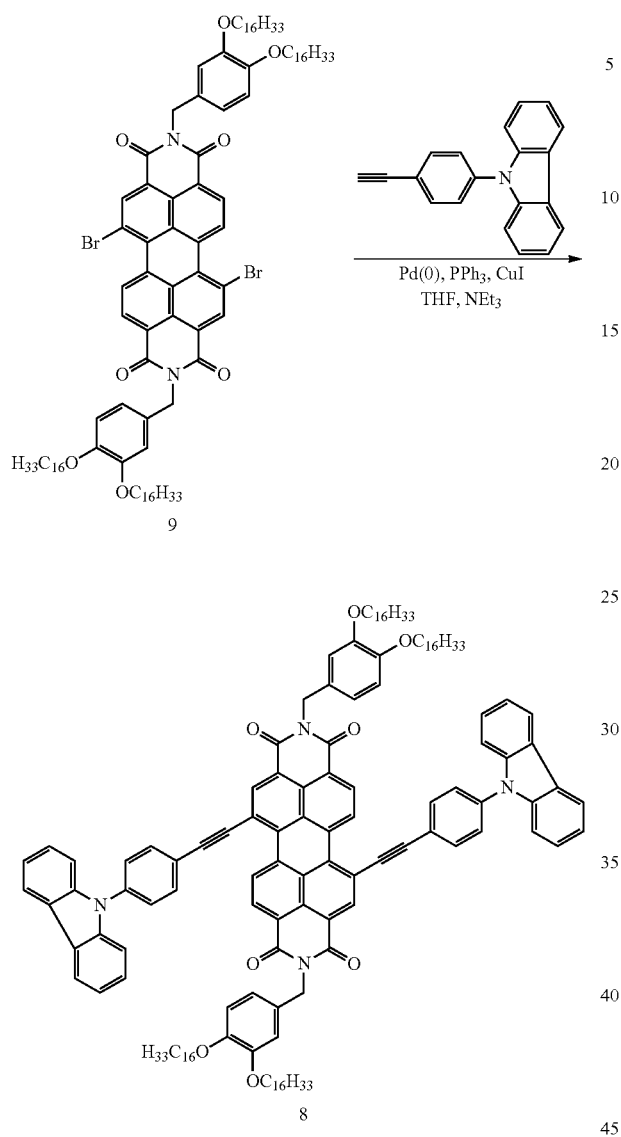

Scheme 3

Diimide 9 (1.8 g), Pd(PPh$_3$)$_2$Cl$_2$ (0.23 g), triphenylphosphine (0.10 g), and CuI (0.06 g) were dissolved in a mixture of NEt$_3$ (40 mL) and THF (60 mL). The resulting solution was degassed several times and then heated at 60° C. for 20 min. 9-(4Ethynylphenyl)carbazole (0.8 g) was added to the solution in one portion under argon atmosphere. Reaction mixture was heated for 2hours and then left at room temperature until completely cooled down. The formed precipitate was filtered out, dried until the constant weight, reprecipitated from CHCl$_3$-MeOH system and the recrystallized from CHCl$_3$. The yield of the organic compound 8 was 1.1 g.

EXAMPLE 2

The example describes synthesis of the organic compound according to the present invention, wherein perylene derivative (structural formula 1) serves as the polycyclic core Cor$_2$, structural formula 20 serves as the polycyclic core Cor1 and phenyl serves as the bridging group B (Scheme 4).

Scheme 4

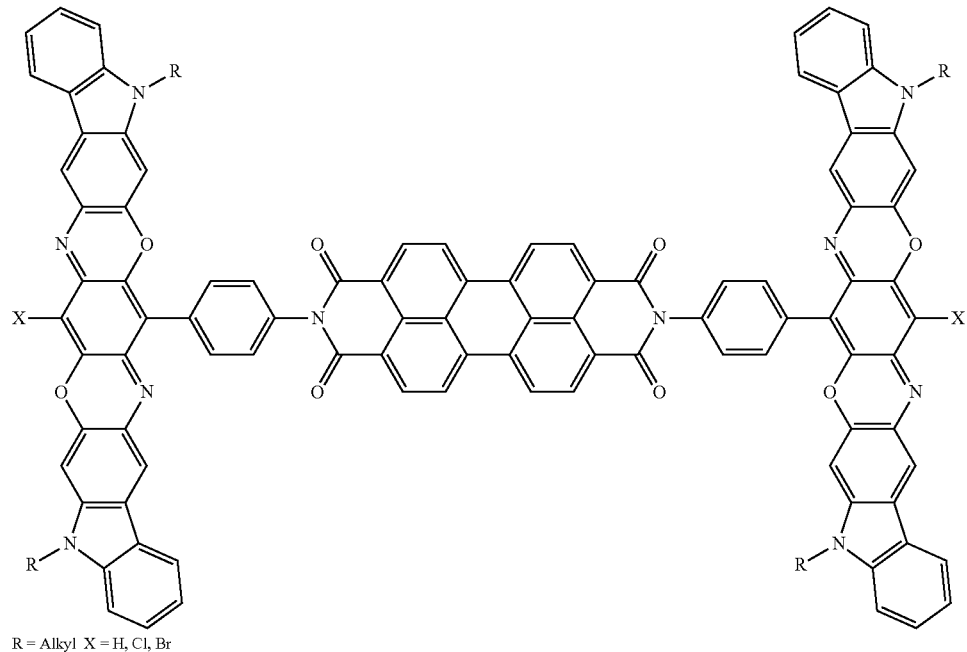

R = Alkyl  X = H, Cl, Br

Synthesis of the above referenced organic compound comprises the following steps:

1. Synthesis of 3-amino-N-alkyl-carbazole 9-alkyl9H-carbazole was synthesized by treatmen-of carbazole with alkyl bromide in the presence of sodium hydride in dimethylformamide (Scheme 5):

Scheme 5

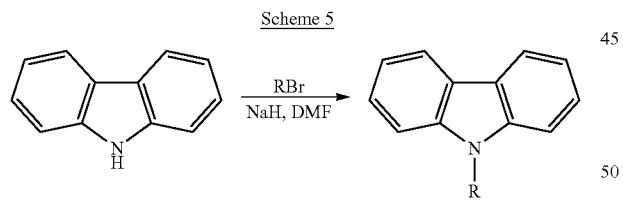

9-alkyl-3-nitro9H-carbazole was prepared by treatment of 9-alkyl-9-carbazole with fuming nitric acid in acetic acid (Scheme 6):

Scheme 6

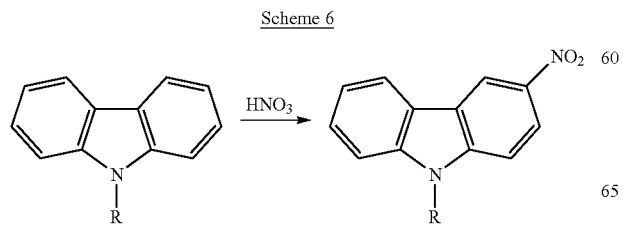

3-amino-N-alkyl-carbazole was prepared by hydrogenation in the presence of 10% palladium on activated carbon powder (Scheme 7);

Scheme 7

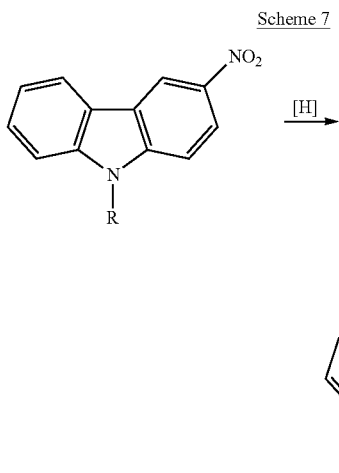

2, Synthesis of Dioxazine Dye 8,18-dibromo-5,15-dialkyl-5,15-dihydrocarbazolo[3',2': 5,6][1,4]oxazino[2,3-b]indolo[2,3-i]phenoxazine (dioxazine fragment) was prepared by condensing and cycling of 3-amino-N-alkyl-carbazole with tetrabromobenzoquinine in o-dichlorobenzene in the presence of benzenesulfochloride (Scheme 8):

Scheme 8

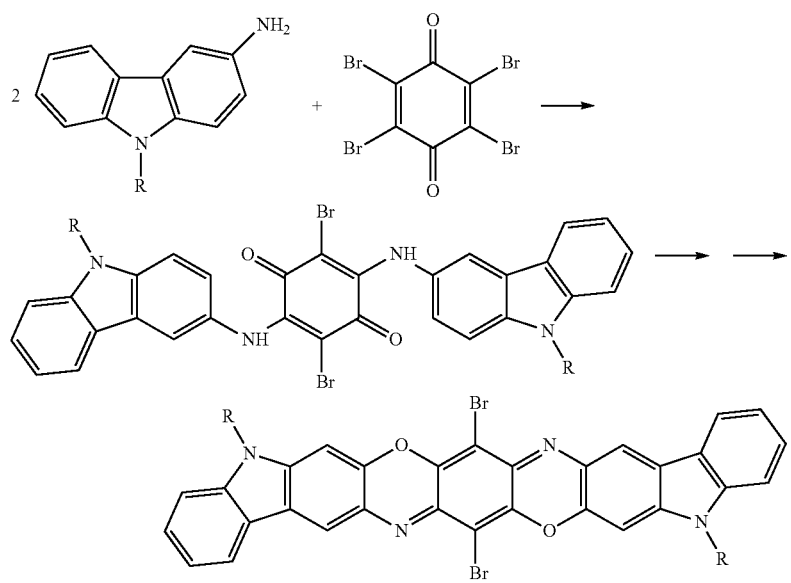

3. Suzuki Coupling 8-bromo5,15-dialkyl-18-(4-nitrophenyl)-5,15-dihydrocarbazolo[3',2':5,6][1,4]oxazino[2,3-b]indolo[2,3-i]phenoxazine was synthesized by Suzuki reaction of 8,18-dibromo-5,15-dialkyl-5,15-dihydrocarbazolo[3',2':5,6][1,4]oxazinol[2,3-b]indolo[2,3-]phenoxazine with (4-nitrophenyl)boronic acid in 1-methyl-2-pyrrolidinone in the presence of tetrakis(triphenylphosphine)palladium(0) (Scheme 9):

Scheme 9

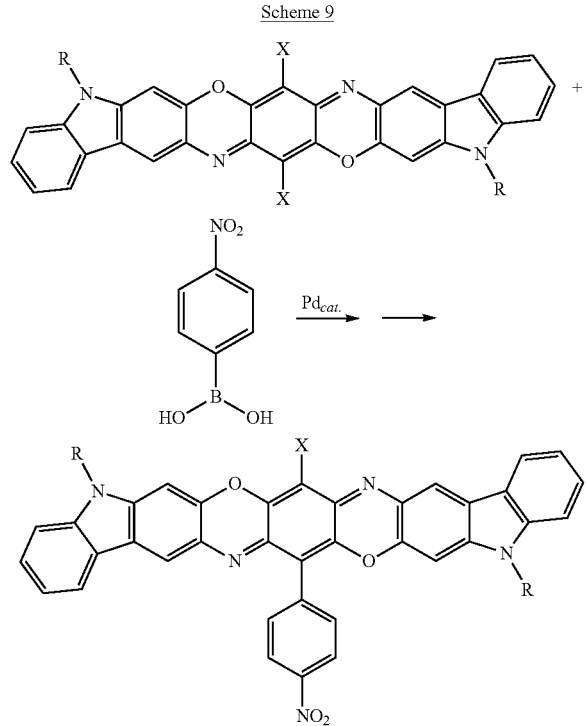

4. Reduction of Nitro-Group 4-(18-bromo-5,15-dialkylyl-5,15-dihydrocarbazolo[3',2':5,6][1,4]oxazino[2,3-b]indolo[2,3-i]phenoxazin-8-yl)aniline was prepared by hydrogenation in the presence of 10% palladium on activated carbon powder (Scheme 10):

Scheme 10

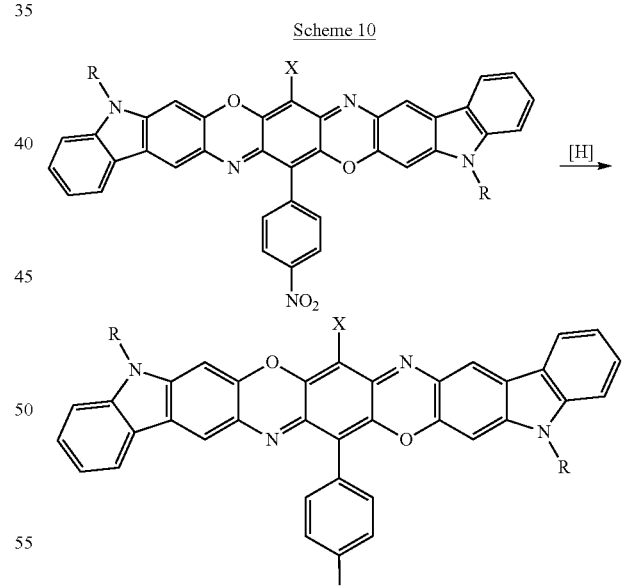

5. Assembling of the Organic Compound

Assembling of the organic compound was done by heating of mixture 4-(18-bromo-5,15-dialkylyl-5,15-dihydrocarbazolo[3',2':5,6][1,4]oxazino-[2,3-b]indolo[2,3-i]phenoxazin-8-yl)aniline and 3,4,9,10-perylenetetracarboxylic dianhydride in 3-chlorophenole (Scheme 11):

Scheme 11

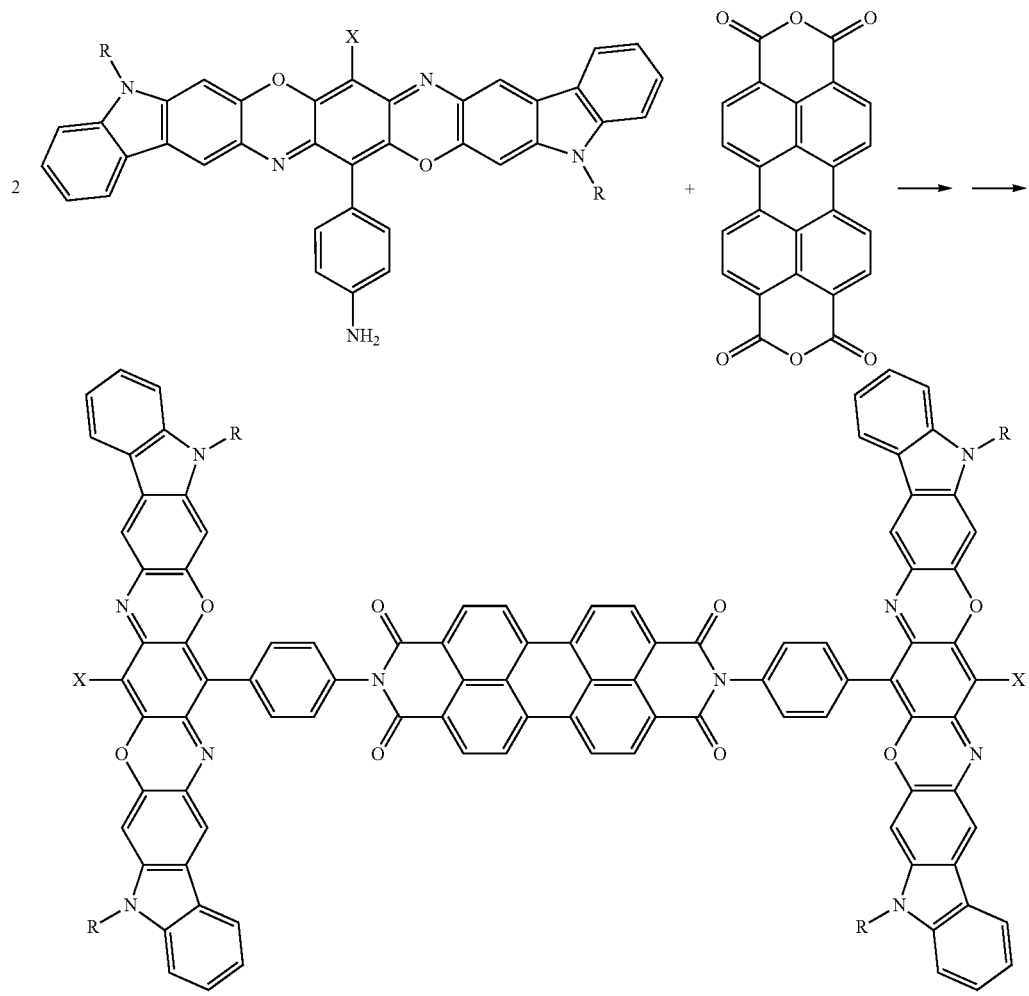

EXAMPLE 3

The Example describes synthesis of the organic compound according to the present invention, wherein perylene derivative (structural formula 1) serves as the polycyclic core Cor$_2$, carbazole (structural formula 19) serves as the polycyclic core Cor1, and biphenyl serves as the bridging group B.

1. Synthesis 3,6-didodecanoylcarbazole

Method is based on acylation of carbazole with dodecanoylchloride under Friedel-Crafts conditions (Scheme 12) and subsequent reduction of two carbonyl groups.

Scheme 12

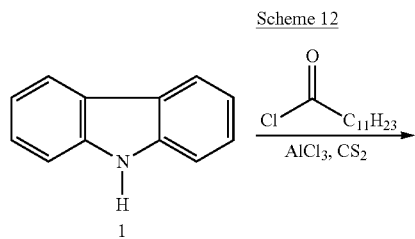

-continued

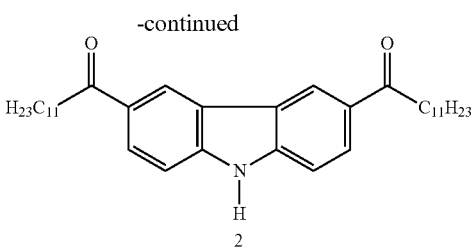

Procedure: A mixture of carbazole (10 g, 60 mmol) and AlCl$_3$, (16.7 g, 127 mmol) in 84 mL of anhydrous CS$_2$, was heated under stirring at reflux temperature and lauroyl chloride (25.2 mL, 122 mmol) added dropwise. The reaction mixture was heated at reflux until ceasing of HCl evolution (3 h) and then the solvent was distilled off. The following procedure steps contained a treatment of the obtained residue with concentrated HCl, dilution with water, filtration of the solid product and washing of the latter on the filter with water. After drying in the air, the crude material was crystallized from ethanol/dioxane to give 1.31 g (Yield: 41.1%) of pure colourless 2, m.p. 179-180° C.

2. Synthesis of 3,6-Didodecylcarbazole

Triethylsilane in trifluoroacetic acid was used for reduction of both carbonyls. The reaction readily occurs at room temperature overnight (Scheme 13).

Scheme 13

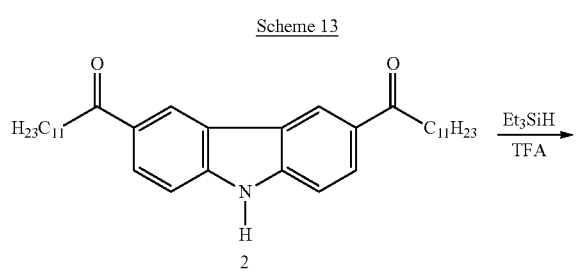

Procedure: Triethylsilane was added drop wise to the solution of 3,6-didodecylcarbazole 3 (10 g) in 100 mil of trifluoroacetic acid at 10° C. The resulting mixture was stirred overnight at room temperature and then 500 ml water was added. The forming precipitate was filtered out, washed with water (3×100 ml) and recrystallized from ethanol to produce 8.0 g of the product.

3. Synthesis of N-(4-nitro)biphenyl-3,6-didodecylcarbazole

For insertion the p-nitrobiphenyl group into 9-position of carbazole the Cu(I)-catalyzed coupling in the presence of potassium, phosphate and trans-1,2-diaminocyclohexane for stabilization the copper(I) was used (Scheme 14).

Procedure: 4-Iodo-4'-nitrobiphenyl (7.5 mmole) 3,6-didodecylcarbazole (9.0 mmol), $K_3PO_4$ (1.58 mmol), CuI (0.16 mmol) and trans-1,2-cyclohexane-diamine (0.90 mmol) were added to 1,4-dioxane (100 ml) at room temperature. The reaction mixture was refluxed for 24 hours. After cooling the mixture to room temperature, the dissolved materials were filtered. 1,4-Dioxane was evaporated, and ethyl acetate was added. The mixture was washed with distilled water, and dried with $MgSO_4$. The final product was obtained through column chromatography (hexane:ethylacetate (9:1). White solid product was obtained (Yield: 90%).

4. Synthesis of N-(4-amino)biphenyl-3,6-didodecylcarbazole

The hydrogenation of nitrogroup was accomplished using palladium/carbon catalysis under hydrogen atmosphere in tetrahydrofuran (Scheme 15).

Scheme 15

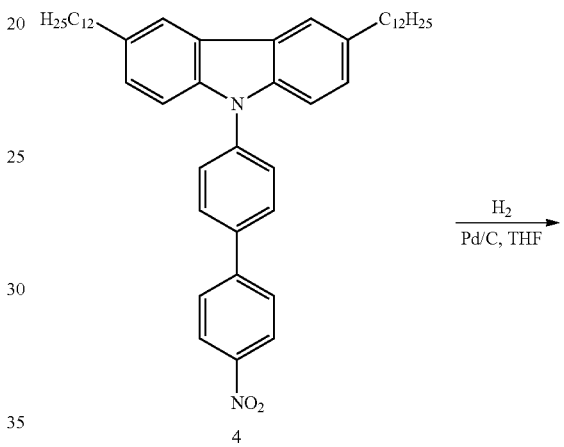

Scheme 14

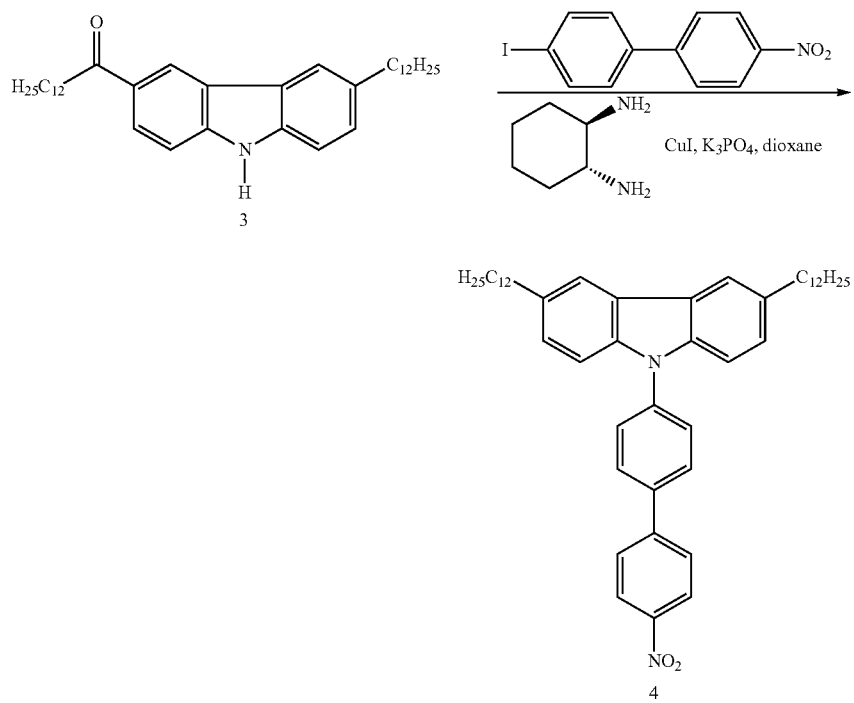

-continued

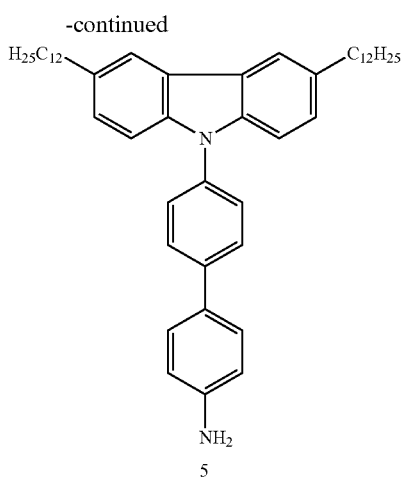

5

Procedure: The solution of N-(4-amino)biphenyl-3,6-didodecylcarbazole (3.1 g) in 80 ml of anhydrous THF was degassed three times using argon, then 0.5 g of Pd/C (10%) was added to the solution. The resulted suspension was degassed again and connected to hydrogen apparatus. The reaction required 8 hours to be completed. The catalyst Pd/C was filtered out and the filtrate was evaporated to afford crude of product. Purification of the product was done using column chromatography on silica gel (ethyl acetate:petroleum ether=1:3). The yield was 2.4 g.

5. Synthesis of Perylene-Based Organic Compound with Carbazole in Apex Position

An assembling of the organic compound was performed in m-chlorophenol (Scheme 16).

Scheme 16

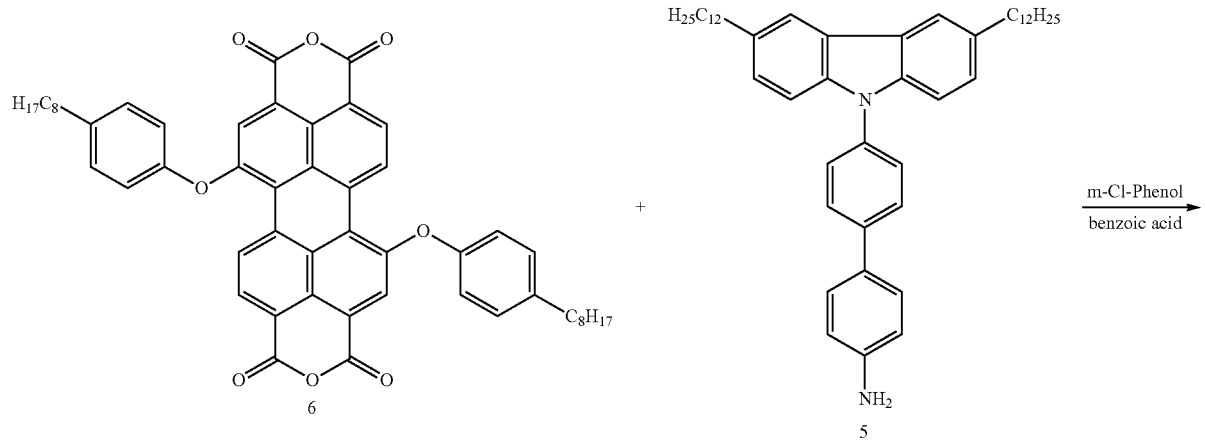

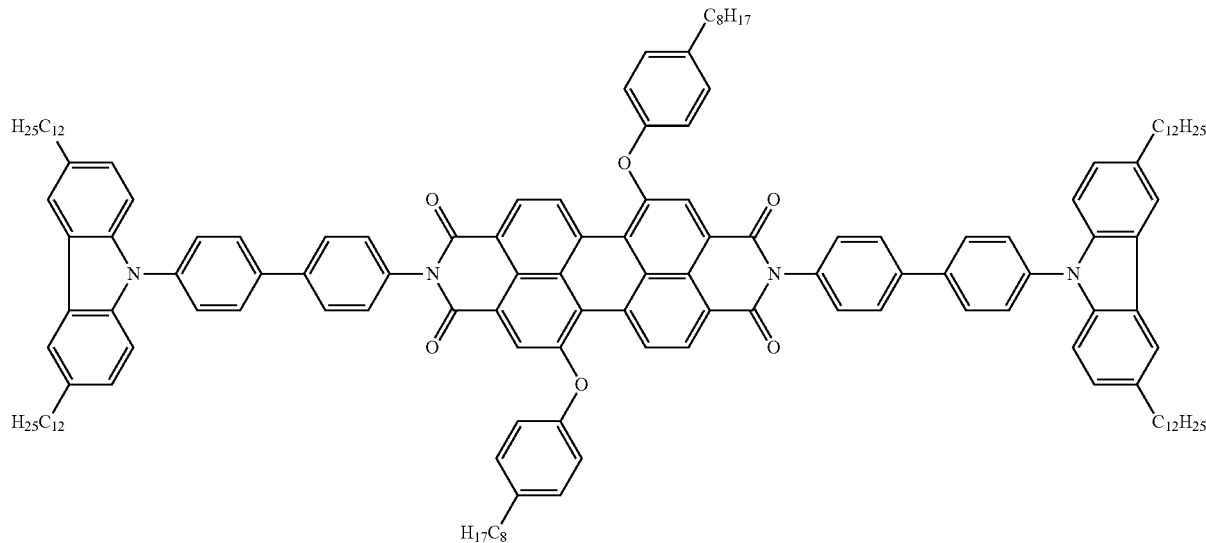

7

Procedure: Amine 5 (1.8 g) was added to a hot (80° C.) solution of perylene 6 (0.8 g) in 10 ml of m-chlorophenol under argon, then 10 mg of benzoic acid was added to the resulting solution. A mixture was stirred at 144° C. for 18 hours (TLC-control). The hot (50° C.) mixture was poured into methanol (150 ml), stirred for 2 hours and filtered out. The precipitate was purified by column chromatography to obtain a pure product using mixture chloroform/petroleum ether (in relation to 2.5:1) as eluent. The product was additionally re-precipitated from methanol-chloroform mixture. The yield of the organic compound 7 was 0.85 g.

EXAMPLE 4

The Example describes synthesis of the organic compound according to the present invention, wherein perylene derivative (structural formula 1) serves as the polycyclic core $Cor_2$, carbazole (structural formula 19) serves as the polycyclic core Cor 1, and phenyl serves as the bridging group B (Scheme 1). Synthesis of this organic compound comprises the following steps:

1. Synthesis of 9-(4-bromophenyl)carbazole (Scheme 17)

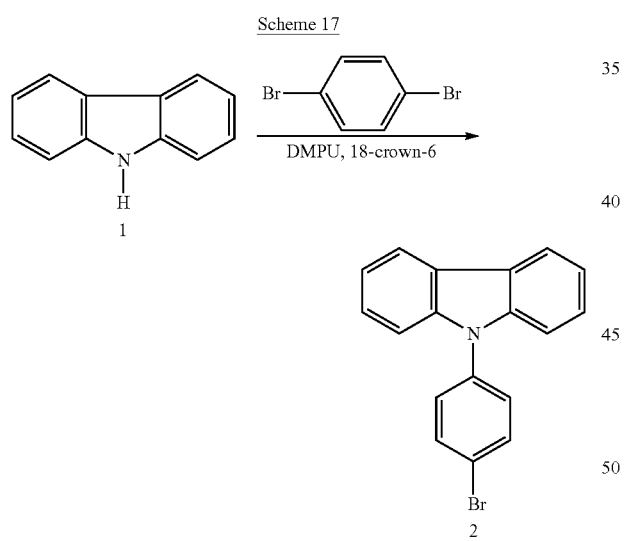

Procedure:

A mixture of CuI (1.14 g, 6 mmol); 18-Crown-6 (0.53 g, 2 mmol), $K_2CO_3$ (16.6 g, 120 mmol), 1,3-dimethyl-3,4,5,6-tetrahydro-2-(1H)-pyrimidinone (DMPU) (2 mL), dibromobenzene (1.42 g, 60 mmol) and carbazole (10 g, 60 mmol) was heated at 170° C. for 11 h under nitrogen. After cooling to room temperature, the mixture was quenched with 1 N HCl, the precipitate was filtered and washed with $NH_4OH$ and water. The grey solid substance was purified with column chromatography using hexane as eluent. The yield was 62%.

2. Synthesis of 9-(4-ethynylphenyl)carbazole (Scheme 18)

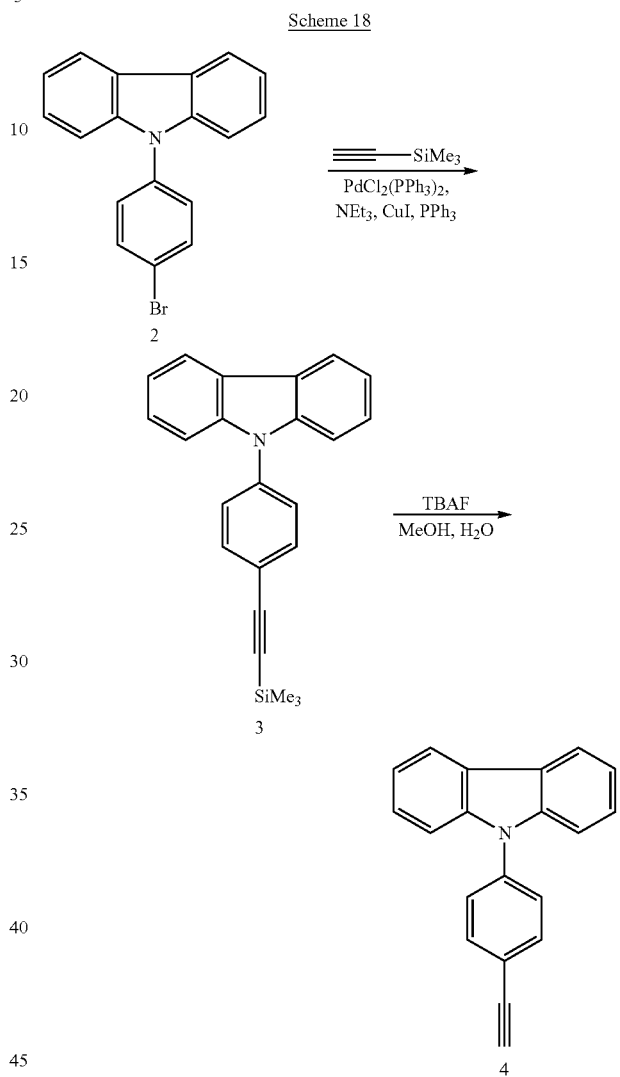

Procedure:

Stage 1: A mixture of 9-(4-bromophenyl)carbazol (4.9 g, 15.3 mmol), trimethylsilylacetylene (2.17 mL), triphenylphosphine (0.19 g), $Pd(PPh_3)_2Cl_2$ (0.12 g) in 60 mL triethylamine was degassed for 15 min. Reaction mixture was boiled for 5 mm, the CUI (0.12 g) was added; the resulted mixture was additionally boiled for 12 hours. After mixture reached room temperature, precipitate was filtered out. Filtrate was evaporated on rotor evaporator, a residue was purified by column chromatography using hexane as eluent and recrystallized from heptane. The yield was 76%.

Stage 2: A mixture of carbazole 3 (2.0 g) and 3 equivalents of tetrabuthylammonium fluoride in 50 mL of anhydrous THF was stirred at room temperature for 12 hours. The resulting mixture was treated with 1N HCl (50 mL) and extracted with ether (2×50 mL). Ether layer was separated and dried over magnesium sulfate, then solvent was removed under reduced pressure and the residue was recrystallized from hexane to produce carbazole 4 with a 65% yield, 3. Synthesis of 1,7-bis[4-carbazole-9-yl)phenyl-4-ethynyl]perylene dianhydride (Scheme 19)
Scheme 19
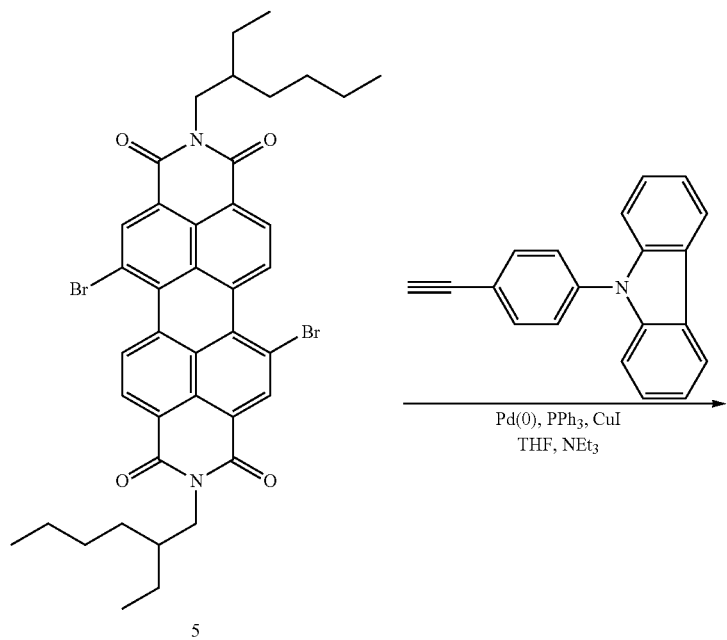
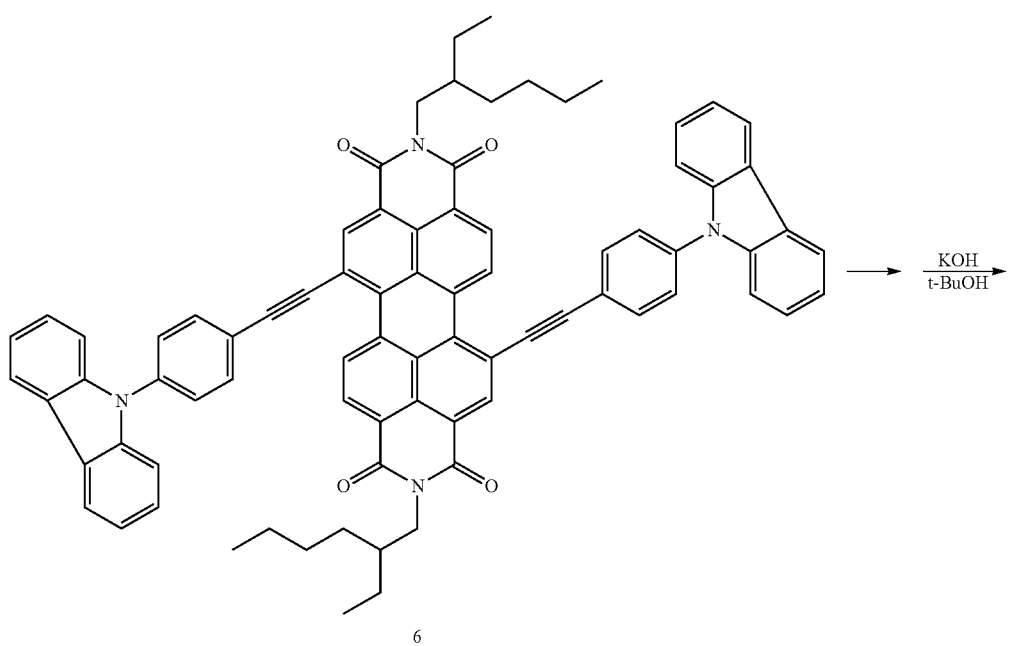

-continued

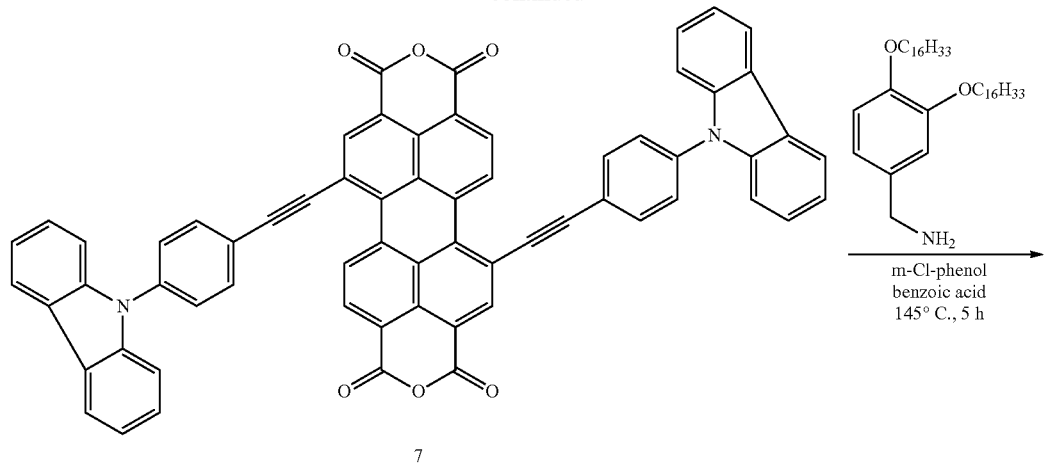

7

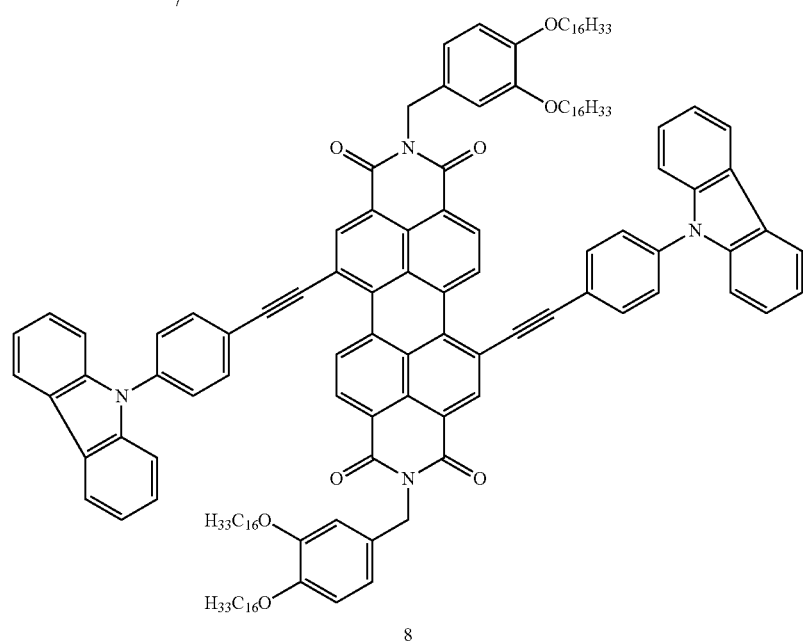

8

Procedure: Procedure for 5:

A mixture of 2-(ethylhexyl)-amine (5.0 g), N-ethylhexyl-1,7-dibromoperylene monoimide (5.0 g) and zinc acetate (0.5 g) in 3-methylphenol (30 mL) was heated at 140° C. for 10 hours. A resulted mixture was allowed to reach 20° C. and poured into 250 mL of 2N HCl. The precipitate was filtered out, washed with ethanol (100 mL) and water (100 mL), dried under vacuum at 100° C. Dried crude of product was additionally washed with hot iso-propanol (2500 ml) and dried again as described above. The yield of pure organic compound 1 was 4.8 g.

Procedure for 6: A mixture of diimide 5 (1.0 g) 9-(4-ethynylphenyl)carbazole (1.4 g), triphenylpbosphine (0.15 g), Pd(PPh$_3$)$_2$Cl$_2$ (0.2 g) NEt$_3$ (20 mL) in 80 mL THF was degassed for 15 min. Reaction mixture was heated for 5 min, the CuI (0.03 g) was added; the resulted mixtureI' was additionally heated for 12 hours. After a mixture reached room temperature, precipitate was filtered out. Filtrate was concentrated to 50 mL on a rotor evaporator and poured out into a mixture ethanol-water (1:1), a resulted precipitate was filtered out and then washed with hot ethanol (100 mL). Combination of these two precipitates was additionally washed with hot ethanol (100 mL) and dried in vacuum at 80° C. for 10 hours to produce the product 6 with the yield of 0.7 g.

Procedure for 7: A solution of 0.65 g of 6, 0.2 g of KOH in 70 ml of t-BuOH was refluxed for 3days until TLC-analysis indicated the full conversion of starting material. Then mixture was poured into hot methanol (100 ml), precipitate was filtered out, dried at 100° C. until the constant weight. The yield of the product 7 was 0.4 g.

Procedure for 8: A mixture of dianhydride 7 (0.4 g), 4 equivalents of 3,4-di(hexadecyloxy)benzylamine, and 10 mg of benzoic acid in 5 ml of m-Cl-phenol was heated at 145°C. for 3 days. TLC-analysis did not register any reaction.

Although the present invention has been described in detail with reference to a particular preferred embodiment, persons possessing ordinary skill in the art to which this invention pertains will appreciate that various modifications and enhancements may be made without departing from the spirit and scope of the claims that follow.

We claim:

1. A photovoltaic layer comprising at least one organic compound having a general structural formula I:

$$\text{Cor}_1\begin{matrix}X^1_p\\ \\R^1_m\end{matrix}-B-\text{Cor}_2\begin{matrix}X^2_q\\ \\R^2_n\end{matrix}-B-\text{Cor}_1\begin{matrix}X^1_p\\ \\R^1_m\end{matrix} \quad (I)$$

where $\text{Cor}_1$ is a polycyclic core of a first type, selected from the list consisting of structures 6-18, and 20:

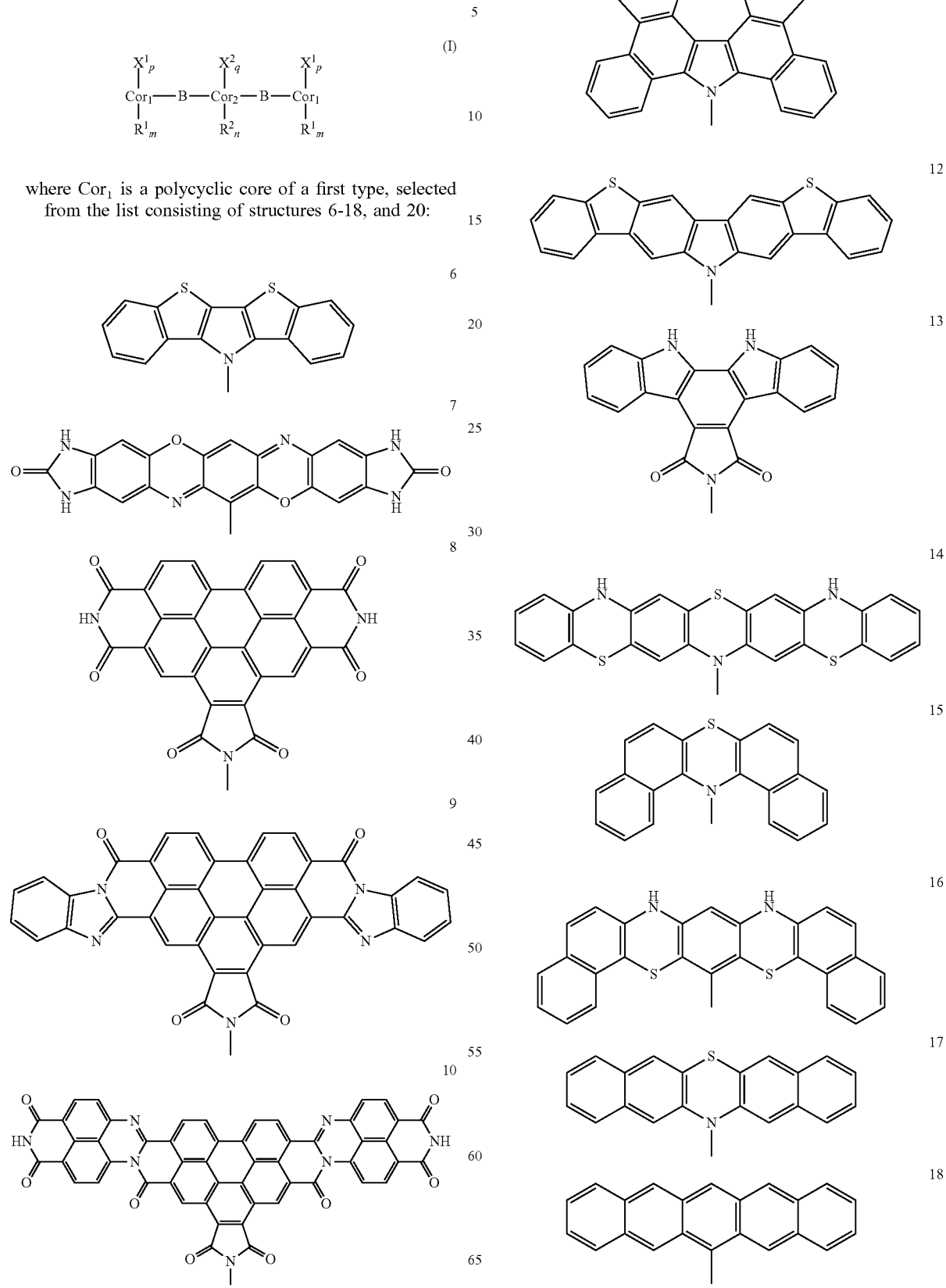

-continued

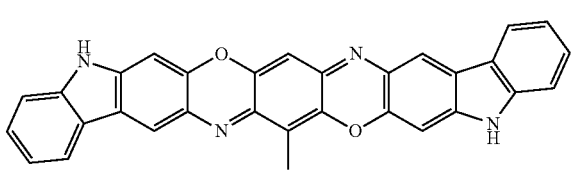

$Cor_2$ is a polycyclic core of a second type, selected from the list consisting of structures 1, 2, and 3:

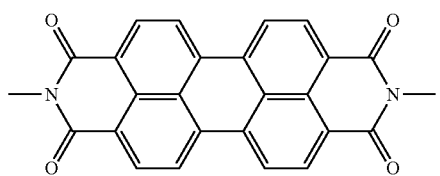

1

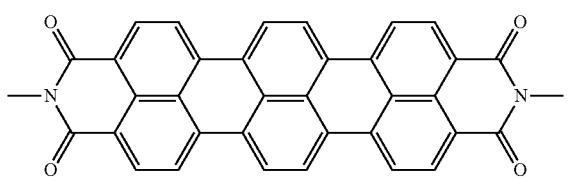

2

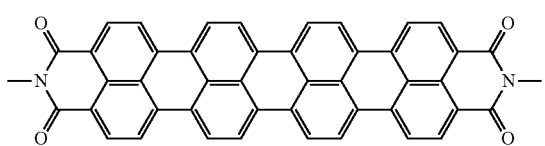

3

B is a bridging group providing a bond of the polycyclic core $Cor_1$ with the polycyclic core $Cor_2$ via covalent chemical bonds, wherein at least one of the bridging groups B is selected from the list consisting of p-phenylene $(Ph_p)$ oligomer, where p is 1, 2, 3, 4 or 5, 2,7-oliqofluorene $(Fl_S)$ oligomer, where s is 1, 2, 3, or 4, and alkylene groups $—(CH_2)_j—$, where j is 1, 2, 3, or 4;

$R^1$ and $R^2$ are molecular groups that are each independently selected from the list consisting of —COOH, —$SO_3H$, and —$H_2PO_3$, linear and branched $(C_1-C_{35})$ alkyl, $(C_2-C_{35})$alkenyl, and $(C_2-C_{35})$alkynyl, substituted alkyl, substituted aryl, and any combination thereof;

the groups $R^1$ and $R^2$ are connected with the cores $Cor_1$ and $Cor_2$ directly or via a spacer selected from the list consisting of aryl, —C(O)—, —C(O)O—, —C(O)NH—, —($SO_2$)NH—, —O—, —$CH_2O$—, —NH—, >N—, and any combination thereof;

m is 1, 2, 3 or 4;

n is 0, 1, 2, 3 or 4;

$X^1$ and $X^2$ are modifying groups which modify energy levels HOMO and LUMO of the polycyclic cores $Cor_1$ and $Cor_2$ ;

p is 0, 1, or 2; and q is 0, 1, or 2;

wherein said organic compound is configured to absorb electromagnetic radiation in at least one predetermined spectral subrange within a wavelength range from 400 to 3000 nm with excitation of electron-hole pairs and dissociation of excited electron-hole pairs; and wherein the polycyclic core $Cor_1$, the bridging group B, and the polycyclic core $Cor_2$ form a molecular system $Cor_1$—B—$Cor_2$B—$Cor_1$ wherein either $Cor_1$ is a donor and $Cor_2$ is an acceptor or $Cor_1$ is an acceptor and $Cor_2$ is a donor.

2. A photovoltaic layer according to claim 1, wherein the polycyclic cores $Cor_1$ and $Cor_2$ assemble into π-π stacks of a first type and a second type that are electrically isolated from each other, wherein the stacks of one type provide electron transport, and the stacks of the other type provide hole transport.

3. A photovoltaic layer according to claim 1, wherein the modifying groups $X^1$ and $X^2$ are selected from the list consisting of H, Cl, Br, F, OH, $NO_2$, NO, and $NH_2$.

4. A photovoltaic layer according to claim 1, wherein at least one of the polycyclic cores $Cor_1$ and $Cor_2$ comprises hetero-atoms selected from the list consisting of nitrogen, oxygen, sulfur, and any combination thereof.

5. A photovoltaic layer according to claim 1, wherein the polycyclic core $Cor_1$ possesses a symmetry of the $C_{2v}$ or $D_{2h}$ space group and the $Cor_2$ possesses a symmetry of the $D_{2h}$ space group.

6. A photovoltaic layer according to claim 1, wherein the molecular system $Cor_1$ —B—$Cor_2$—B—$Cor_1$ possesses a symmetry of the $D_{2h}$ space group.

7. A photovoltaic layer according to claim 1, wherein the energy levels of donors are correlated with energy levels of acceptor according to the following equations: $HOMO_A < HOMO_D \leq (LUMO_A-1$ eV$)$ and $LUMO_A < LUMO_D$.

8. A photovoltaic layer according to claim 1, wherein the $Cor_2$ is perylene diimide and serves as the acceptor core, the bridging group B is selected from the list consisting of phenyl and biphenyl, the $Cor_1$ is the donor, and the energy levels $HOMO_D$ and $LUMO_D$ of donor cores $Cor_1$ satisfy to the following conditions: −6.0 eV <$HOMO_{D<-}$5.5 eV and −4.0 eV <$LUMO_D$.

9. A photovoltaic layer according to claim 8, wherein the organic compound is selected from the list consisting of structures 21, 22, 23, 24, and 26:

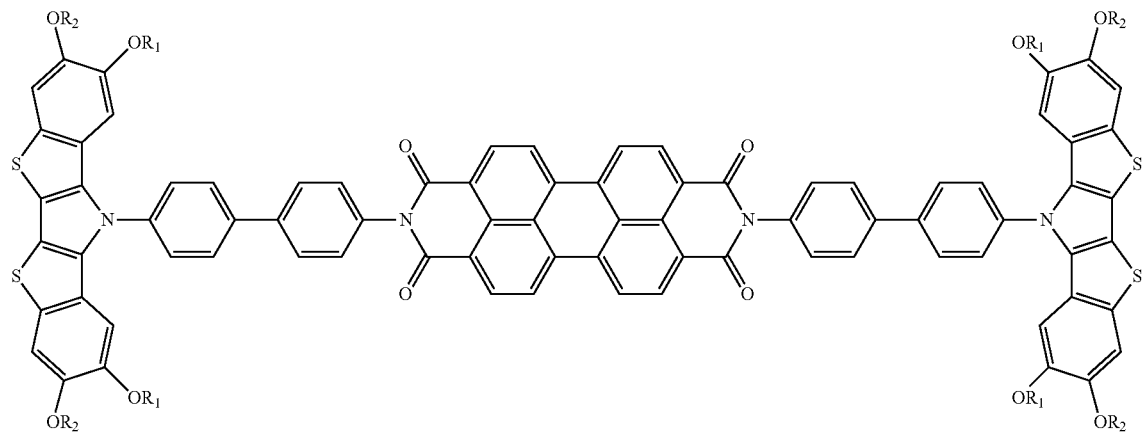
21
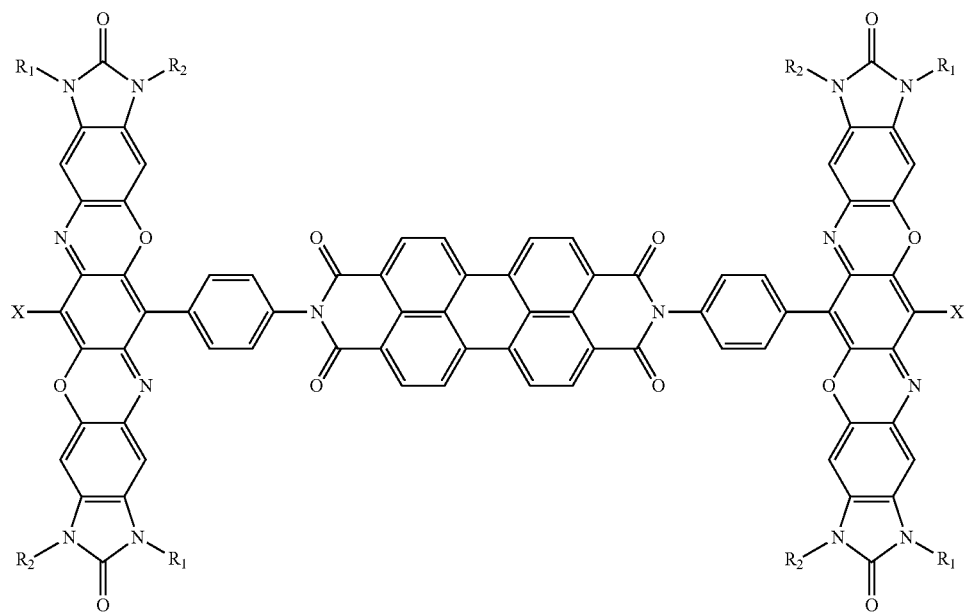
22
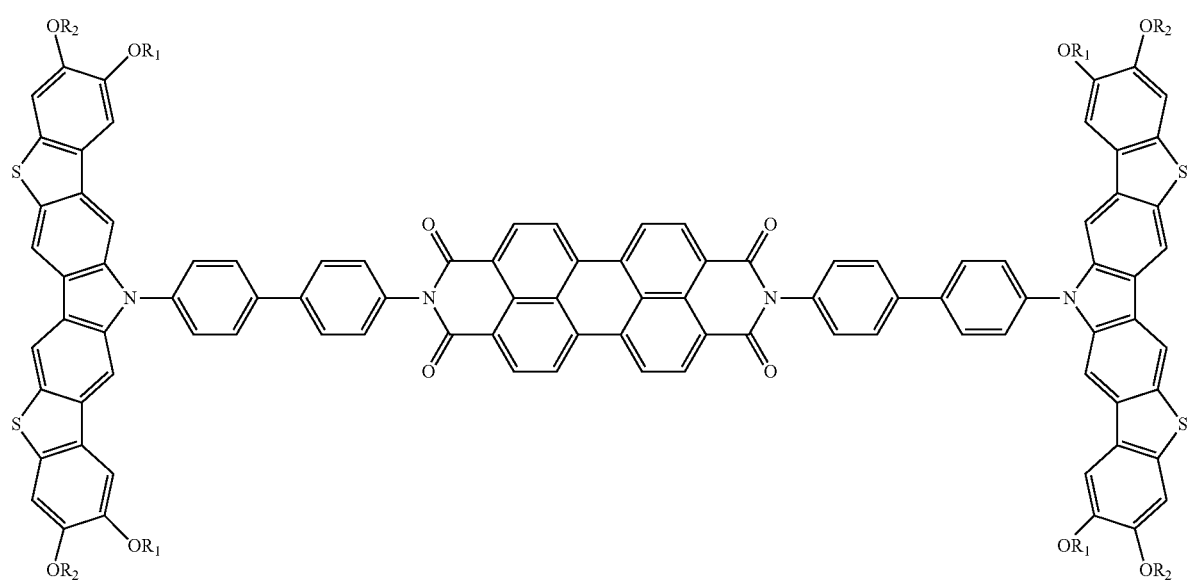
23

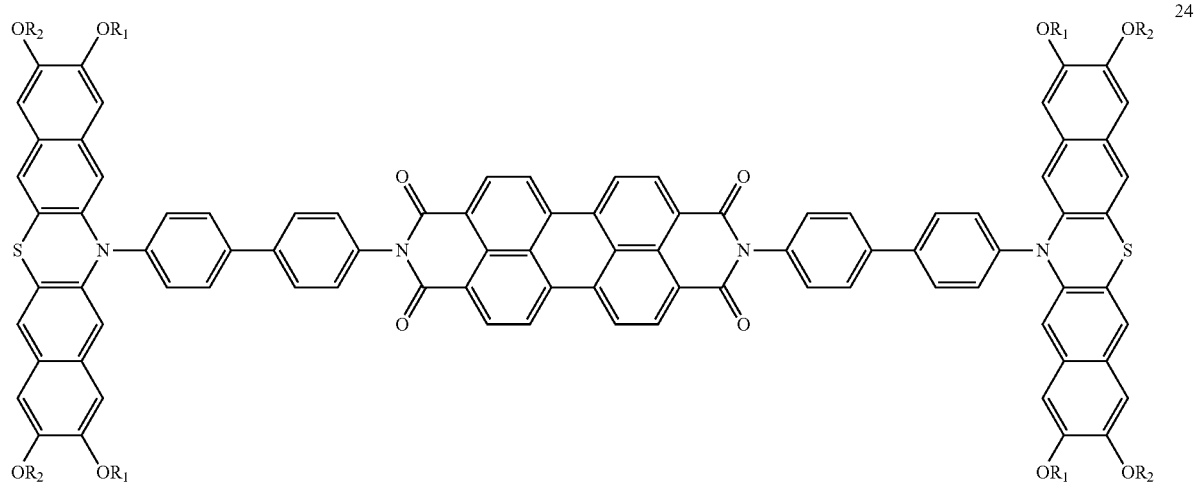

24

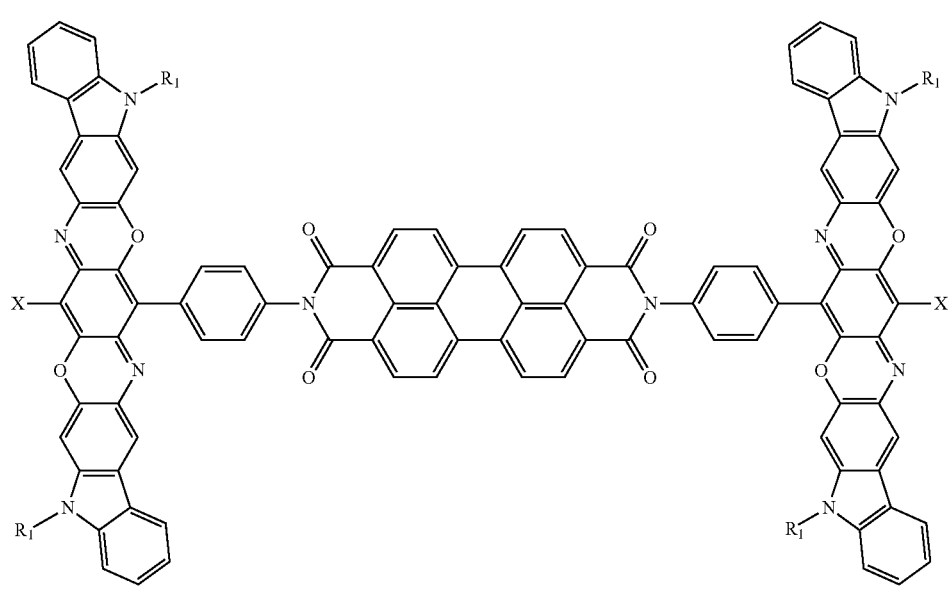

26 and X is Cl or Br.

10. A photovoltaic layer according to claim 1, wherein the photovoltaic layer is placed on a substrate made of material transparent for the incident electromagnetic radiation to which said organic compound is sensitive.

11. A photovoltaic device comprising a first and a second electrode, and at least one photovoltaic layer, wherein the photovoltaic layer has a front surface and a rear surface and comprises at least one organic compound of structural formula I:

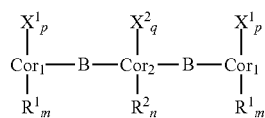

(I)

where $Cor_1$ is a polycyclic core of a first type, selected from the list consisting of structures 6-18, and 20:

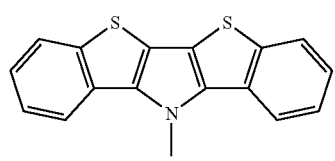

6

7

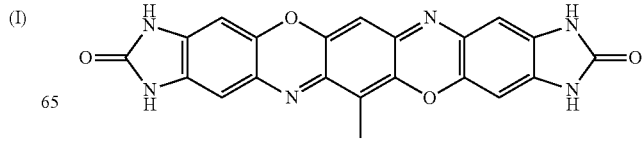

Cor₂ is a polycyclic core of a second type, selected from the list consisting of structures 1, 2, and 3:

-continued

3

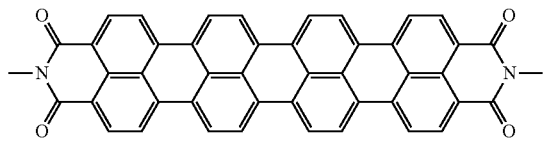

B is a bridging group providing a bond of the polycyclic core $Cor_1$ with the polycyclic core $Cor_2$ via covalent chemical bonds, wherein at least one of the bridging groups B is selected from the list consisting of p-phenylene ($Ph_p$) oligomer, where p is 1, 2, 3, 4 or 5, 2,7-oligofluorene ($Fl_s$) oligomer, where s is 1, 2, 3, or 4, and alkylene groups —$(CH_2)_j$—, where j is 1, 2, 3, or 4;

$R^1$ and $R^2$ are molecular groups that are each independently selected from the list consisting of —COOH, —$SO_3H$, and —$H_2PO_3$, linear and branched ($C_1$-$C_{35}$)alkyl, ($C_2$-$C_{35}$)alkenyl, and ($C_2$-$C_{35}$)alkynyl, substituted alkyl, substituted aryl, and any combination thereof;

the groups $R^1$ and $R^2$ are connected with the cores $Cor_1$ and $Cor_2$ directly or via a spacer selected from the list consisting of aryl, —C(O)—, —C(O)O—, —C(O)—NH—, —($SO_2$)NH—, —O—, —$CH_2$O—, —NH—, >N—, and any combination thereof;

m is 1, 2, 3 or 4;

n is 0, 1, 2, 3 or 4;

$X^1$ and $X^2$ are modifying groups which modify energy levels HOMO and LUMO of the polycyclic cores $Cor_1$ and $Cor_2$;

p is 0, 1, or 2; and q is 0, 1, or 2;

wherein said organic compound absorbs electromagnetic radiation in at least one predetermined spectral sub-range within a wavelength range from 400 to 3000 nm with excitation of electron-hole pairs and dissociation of excited electron-hole pairs; and wherein the polycyclic core $Cor_1$, the bridging group B, and the polycyclic core $Cor_2$ form a molecular system $Cor_1$—B—$Cor_2$—B—$Cor_1$ wherein either $Cor_1$ is a donor and $Cor_2$ is an acceptor or $Cor_1$ is an acceptor and $Cor_2$ is a donor.

12. A photovoltaic device according to claim 11, wherein the first electrode is formed on at least a part of the front surface of said photovoltaic layer, and the second electrode is formed on at least a part of the rear surface of said photovoltaic layer.

13. A photovoltaic device according to claim 11, wherein the second electrode is a reflective electrode for the electromagnetic radiation incident upon the device.

14. A photovoltaic device according to claim 11, wherein one of the electrodes is made of a material that provides a hole-harvesting contact and a barrier contact for electrons, and the other electrode is made of a material that provides a barrier contact for holes and an electron-harvesting contact.

15. A photovoltaic device according to claim 14, wherein the electrode material is selected from the list consisting of: aluminium, indium tin oxide (ITO), a carbon nanotube conductive coating, a PEDOT:PSS layers, a phthalocyanine, LiF, and aluminium-doped zinc oxide.

16. A photovoltaic device according to claim 11, wherein one of the electrodes comprises an electron-acceptor layer contacting with the photovoltaic layer, and the other electrode comprises an electron-donor layer contacting with the photovoltaic layer.

17. A photovoltaic device according to claim 11, further comprising a substrate bearing said electrodes and said photovoltaic layer, wherein the substrate is transparent for the incident electromagnetic radiation to which said device is sensitive.

18. A photovoltaic device according to claim 11 comprising two or more said photovoltaic layers, wherein said photovoltaic layers comprise different organic compounds of general structural formula (I).

* * * * *